US012690994B2

(12) United States Patent
Schreck

(10) Patent No.: US 12,690,994 B2
(45) Date of Patent: Jul. 28, 2026

(54) BIFURCATED BALLOON CATHETERS AND METHODS OF USE

(71) Applicant: Restore Endosystems, LLC, South Jordan, UT (US)

(72) Inventor: Stefan Georg Schreck, South Jordan, UT (US)

(73) Assignee: Restore Endosystems, LLC, Trabuco Canyon, CA (US)

( * ) Notice: Subject to any disclaimer, the term of this patent is extended or adjusted under 35 U.S.C. 154(b) by 649 days.

(21) Appl. No.: 18/067,321

(22) Filed: Dec. 16, 2022

(65) Prior Publication Data

US 2023/0190501 A1 Jun. 22, 2023

Related U.S. Application Data

(60) Provisional application No. 63/291,190, filed on Dec. 17, 2021.

(51) Int. Cl.
*A61F 2/954* (2013.01)
*A61F 2/958* (2013.01)
*A61M 25/10* (2013.01)

(52) U.S. Cl.
CPC .............. *A61F 2/954* (2013.01); *A61F 2/958* (2013.01); *A61M 2025/1045* (2013.01)

(58) Field of Classification Search
CPC .. A61F 2/954; A61F 2/958; A61M 2025/1045
See application file for complete search history.

(56) References Cited

U.S. PATENT DOCUMENTS

| | | | |
|---|---|---|---|
| 5,824,055 A | 10/1998 | Spiridigliozzi et al. | |
| 6,017,324 A | 1/2000 | Tu et al. | |
| 6,045,557 A | 4/2000 | White et al. | |
| (Continued) | | | |

FOREIGN PATENT DOCUMENTS

| | | | |
|---|---|---|---|
| CN | 102470029 A | 5/2012 | |
| EP | 0965311 A2 | 12/1999 | |
| (Continued) | | | |

OTHER PUBLICATIONS

International Search Report and Written Opinion dated Jan. 14, 2022 for PCT/US2021/054258.

(Continued)

*Primary Examiner* — Melanie R Tyson
(74) *Attorney, Agent, or Firm* — Dorsey & Whitney LLP

(57) ABSTRACT

Balloon catheters for treating a diseased bifurcated blood vessel that includes a catheter hub, a proximal balloon hub, a distal balloon hub, a catheter tip, a catheter shaft comprising a proximal shaft and a distal shaft, and a bifurcated balloon assembly with a first balloon and second balloon that are substantially parallel. A proximal end of the proximal shaft is connected to the catheter hub and a distal end of the proximal shaft is connected to the proximal balloon hub. A proximal end of the distal shaft is connected to the distal balloon hub and a distal end of the distal shaft is connected the catheter tip. A proximal end of the first balloon is connected to the proximal balloon hub, a distal end of the first balloon is connected to the distal balloon hub, and a distal end of the second balloon is connected to the distal balloon hub.

18 Claims, 49 Drawing Sheets

(56) References Cited

U.S. PATENT DOCUMENTS

| | | | |
|---|---|---|---|
| 6,086,611 | A | 7/2000 | Duffy et al. |
| 6,099,497 | A | 8/2000 | Adams et al. |
| 6,165,195 | A | 12/2000 | Wilson |
| 6,355,061 | B1 | 3/2002 | Quiachon et al. |
| 6,537,284 | B1 | 3/2003 | Inoue |
| 6,558,396 | B1 | 5/2003 | Inoue |
| 7,959,667 | B2 | 6/2011 | Ta et al. |
| 8,257,431 | B2 | 9/2012 | Henderson et al. |
| 9,539,083 | B2 | 1/2017 | Krimsky et al. |
| 10,219,926 | B2 | 3/2019 | Bourang et al. |
| 2002/0077692 | A1 | 6/2002 | Besselink |
| 2004/0049204 | A1 | 3/2004 | Harari et al. |
| 2004/0127850 | A1 | 7/2004 | Steadham et al. |
| 2004/0148007 | A1 | 7/2004 | Jackson et al. |
| 2004/0176837 | A1 | 9/2004 | Atladottir et al. |
| 2004/0200978 | A1 | 10/2004 | Kamijo |
| 2005/0043784 | A1 | 2/2005 | Yampolsky et al. |
| 2005/0149168 | A1 | 7/2005 | Gregorich |
| 2005/0192656 | A1 | 9/2005 | Eidenschink |
| 2005/0228472 | A1 | 10/2005 | Case et al. |
| 2006/0212113 | A1 | 9/2006 | Shaolian et al. |
| 2007/0118165 | A1 | 5/2007 | Demello et al. |
| 2007/0142819 | A1 | 6/2007 | El-Nounou et al. |
| 2007/0168020 | A1 | 7/2007 | Brucker et al. |
| 2007/0213802 | A1 | 9/2007 | Von et al. |
| 2007/0270769 | A1 | 11/2007 | Wilson et al. |
| 2007/0299495 | A1 | 12/2007 | Zukowski et al. |
| 2008/0051869 | A1 | 2/2008 | Yribarren |
| 2008/0103587 | A1 | 5/2008 | Henderson et al. |
| 2008/0114438 | A1 | 5/2008 | Hartley et al. |
| 2008/0125847 | A1 | 5/2008 | Krever et al. |
| 2008/0133000 | A1 | 6/2008 | Molony |
| 2009/0012601 | A1 | 1/2009 | Siu et al. |
| 2009/0124968 | A1 | 5/2009 | Goshgarian |
| 2009/0204083 | A1 | 8/2009 | Odonnell et al. |
| 2009/0259288 | A1 | 10/2009 | Wijay et al. |
| 2009/0259293 | A1 | 10/2009 | Moloney |
| 2009/0299453 | A1 | 12/2009 | Arcand et al. |
| 2010/0106238 | A1 | 4/2010 | Hilaire et al. |
| 2011/0208286 | A1 | 8/2011 | Ta et al. |
| 2013/0053940 | A1 | 2/2013 | Suhr |
| 2013/0123907 | A1 | 5/2013 | Roeder et al. |
| 2013/0296997 | A1 | 11/2013 | Kamat |
| 2014/0214002 | A1 | 7/2014 | Lieber et al. |
| 2014/0277353 | A1 | 9/2014 | Hartley |
| 2014/0324150 | A1 | 10/2014 | Stephens et al. |
| 2015/0126986 | A1* | 5/2015 | Kelly ............... A61B 18/02 |
| | | | 606/23 |
| 2015/0250579 | A1 | 9/2015 | Howard et al. |
| 2015/0289875 | A1 | 10/2015 | Consigny et al. |
| 2017/0007431 | A1 | 1/2017 | Al-Saadon |
| 2018/0015264 | A1 | 1/2018 | Wang et al. |
| 2020/0375724 | A1 | 12/2020 | Perkins et al. |
| 2021/0401566 | A1 | 12/2021 | Geusen et al. |
| 2022/0077692 | A1 | 3/2022 | Myers et al. |
| 2022/0387200 | A1 | 12/2022 | Kamat |
| 2023/0144448 | A1 | 5/2023 | Schreck |
| 2023/0146392 | A1 | 5/2023 | Mottola et al. |
| 2023/0210679 | A1 | 7/2023 | Schreck |
| 2024/0156622 | A1 | 5/2024 | Hall et al. |
| 2024/0156627 | A1 | 5/2024 | Adams et al. |

FOREIGN PATENT DOCUMENTS

| | | |
|---|---|---|
| EP | 1920734 A2 | 5/2008 |
| EP | 2068761 B1 | 2/2019 |
| JP | 2003502080 A | 1/2003 |
| WO | 2000027307 | 5/2000 |
| WO | 0143665 A2 | 12/2000 |
| WO | 2009131309 A2 | 10/2009 |
| WO | 2022060994 A1 | 3/2022 |

OTHER PUBLICATIONS

International Search Report and Written Opinion dated Apr. 19, 2023 for PCT/US2022/081847.
International Search Report and Written Opinion dated Feb. 4, 2022 for PCT/US2021/050688.
European Search Report dated Aug. 22, 2024 for EP21870220.7.
Partial European Search Report dated Sep. 25, 2024 for EP21878652.3.
International Search Report and Written Opinion dated Mar. 20, 2024 for PCT/US2023/079678.
International Search Report and Written Opinion dated Apr. 24, 2024 for PCT/US2023/079627.
European Search Report dated Dec. 16, 2024 for EP21878652.3.
Extended European Search Report dated Sep. 24, 2025 for EP22908768.9.
Office Action dated Nov. 4, 2025 for U.S. Appl. No. 18/177,027.
Office Action dated Jan. 28, 2026 for U.S. Appl. No. 17/929,260.
Office Action dated Mar. 11, 2026 for U.S. Appl. No. 18/508,539.
Notice of Allowance dated Mar. 16, 2026 for U.S. Appl. No. 18/177,027.
Office Action dated Mar. 24, 2026 for U.S. Appl. No. 18/509,005.
Notice of Allowance dated May 12, 2026 for U.S. Appl. No. 17/929,260.

* cited by examiner

BIFURCATED BALLOON CATHETERS AND METHODS OF USE

RELATED CASES

This application claims priority to U.S. Provisional Application No. 63/291,190, filed on Dec. 17, 2021 and titled "BIFURCATED BALLOON CATHETERS AND METHODS OF USE," which is hereby incorporated by reference in its entirety.

FIELD

Bifurcated balloon catheters and methods of using the same are described herein.

BACKGROUND

Aorto-iliac occlusive disease (AIOD) refers to narrowing or stenosis of the blood vessels involving the infrarenal aorta and the two iliac arteries. In complex cases the aorto-iliac bifurcation may be involved.

Balloon angioplasty and placement of bare or covered stents are current methods of treating local narrowing or occlusions of arteries. The "kissing-balloon" technique, the "kissing-stent" technique, and the Covered Endovascular Reconstruction of Aortic Bifurcation (CERAB) technique have been developed to treat AOID involving the aorto-iliac bifurcation. These three methods include simultaneous placement of two parallel "kissing" balloons across the bifurcation. A shortcoming of these techniques is the need for accurate simultaneous placement and inflation of the two kissing balloons. Another shortcoming is that the balloons form a dual double barrel in the aorta and do not conform to the aortic wall. An additional shortcoming of the two-stenting technique is the disruption of the natural blood flow through the bifurcation that can lead to thrombus formation, hemolysis, emboli and restenosis. Another shortcoming is the technical skill set required to perform these procedures. Even further yet, another shortcoming is that the two stenting technique makes re-intervention procedures using a retrograde approach (up- and over technique) challenging.

As an alternative approach, self-expanding bifurcated stent grafts (e.g., AFX device manufactured by Endologix) have been placed to treat complex aorto-iliac disease. The advantage of the bifurcated stent graft is that it preserves the bifurcation avoiding flow disturbances and allowing for a retrograde approach for re-intervention. A shortcoming of this approach is that the self-expanding stent may have insufficient outward force to maintain flow. Another shortcoming is the large profile (cross-sectional area) of the delivery system. A third shortcoming is the exposed stent structures of the AFX device that can lead to flow disruptions, thrombus formation and difficulties with future crossover interventions. Another shortcoming is the complex procedural steps and high technical skill set that is required to place the AFX device in a diseased aorto-iliac bifurcation. Further yet, another shortcoming is the difficulty to accurately size self-expanding stents to the variability in aortic and iliac diameters, which can lead to infolding and blood flow disturbances and/or a lack of vessel wall apposition. Other self-expanding abdominal aortic aneurysm stent grafts are sometimes used to treat aortoiliac occlusive disease, but they have similar shortcomings as the AFX system.

There is a need for medical devices and methods for the treatment of AIOD involving the aorto-iliac bifurcation that can overcome the above listed shortcomings of existing methods.

BRIEF SUMMARY

Described herein are bifurcated balloon catheter systems and methods for the treatment of branching blood vessels. The systems can be introduced percutaneously or by surgical cutdown into a patient's arterial system. The bifurcation from the aorta to the iliac arteries (aortoiliac bifurcation) is used as an example of a branching blood vessel which can be treated with the systems described herein. It is understood that the application of the systems described herein are not limited to the aorto-iliac bifurcation. The systems and methods of use described herein can be applied to any branching or bifurcated artery, vein, or airway in a body. In some embodiments, the body is the body of a mammal. In other embodiments, the mammal is a human. The words systems, devices, medical devices, and/or apparatuses are used herein interchangeably.

For consistency, when describing the systems, the direction toward the external end of the system outside the body is referred to as "proximal" and the direction away from the external end of the system is referred to as "distal". The side on which the system is inserted into the arteries is referred to as "ipsilateral", the opposite side is referred to as "contralateral". For example, if the system is inserted into an artery of the right leg, the right side of the body is referred to as ipsilateral and the right iliac artery is referred to as the ipsilateral iliac artery. The left side is referred to as contralateral and the left iliac artery is referred to as the contralateral iliac artery.

In some embodiments, the present disclosure includes a balloon catheter for the treatment of a bifurcated vessel. The balloon catheter can be used to perform an angioplasty of the diseased bifurcated vessel. The balloon catheter can be used to deploy a cylindrical or a bifurcated stent into a bifurcated vessel. The balloon catheter can be used to deploy a cylindrical or a bifurcated covered stent into a bifurcated vessel. The balloon catheter can be used to deliver a therapeutic agent to the walls of the bifurcated vessel. The balloon catheter can be used to deliver energy to the walls of the bifurcated vessel. The balloon catheter can be used to temporarily occlude the bifurcated vessel.

In some embodiments, a balloon catheter for performing an angioplasty of the aorto-iliac bifurcation or for placing a bifurcated stent into the aorto-iliac bifurcation is disclosed. The balloon catheter comprises a catheter hub, a proximal and distal balloon hub, a proximal and a distal shaft, and a bifurcated balloon assembly located between the proximal and the distal balloon hub. The balloon assembly comprises of two cylindrical balloons which are arranged substantially in parallel to each other: a first (ipsilateral) balloon that is connected on the proximal end to the proximal balloon hub and on the distal end to the distal balloon hub, and a second (contralateral) balloon that has a free proximal end and is connected on the distal end to the distal balloon hub. In some embodiments, the balloon assembly comprises an additional restraining sleeve that is placed over the distal sections of both balloons.

The balloon catheter includes a bifurcated inflation lumen that extends from the catheter hub to the distal balloon hub and has a branch from the distal balloon hub to the contralateral balloon. The bifurcated inflation lumen is connected to an inflation port within the catheter hub and is in fluid communication with the first and the second balloon. The balloon catheter can include a second bifurcated lumen that extends from the catheter hub to the distal shaft and has a branch from the distal balloon hub through the contralateral balloon shaft. The second bifurcated lumen includes a contralateral guidewire assembly having a first proximal end that exits the balloon catheter at the catheter hub and a second proximal end that exits the balloon catheter at the free proximal end of the second (contralateral) balloon, and a distal end that is housed within the distal shaft. The first proximal end of the contralateral guidewire assembly is connected to a contralateral actuator handle. The second contralateral proximal end has a flexible radiopaque guidewire tip for advancing the guidewire atraumatically through the vasculature. Rotating the contralateral actuator handle rotates the contralateral guidewire tip. Moving the contralateral actuator handle proximally moves the contralateral guidewire tip proximally and moving the contralateral actuator handle distally moves the contralateral guidewire tip distally.

The balloon catheter can include a multi-purpose lumen extending from a port in the catheter hub to the proximal balloon hub. The multi-purpose lumen can house the tip of the contralateral guidewire during device insertion. The multi-purpose lumen can provide a pathway for a tether wire that is connected at its proximal end to a tether handle and on the distal end to the free proximal end of the contralateral balloon. The multi-purpose lumen can provide a pathway for a snare to capture the tip of the contralateral guidewire. The multi-purpose lumen can provide a pathway for injecting contrast medium into the blood stream.

In other embodiments, a protective sheath can be mounted onto the balloon catheter to facilitate the passage of the balloon catheter through an introducer sheath or guide catheter. The protective sheath is inserted past the hemostasis valve of the introducer sheath or guide catheter and prevents the hemostasis valve from engaging with the balloon catheter.

In one embodiment, a balloon catheter for treating a diseased bifurcated blood vessel is described. The balloon catheter comprises a catheter hub; a proximal balloon hub; a distal balloon hub; a catheter tip; a catheter shaft comprising a proximal shaft and a distal shaft, wherein the proximal end of the proximal shaft is connected to the catheter hub and the distal end of the proximal shaft is connected to the proximal balloon hub, the proximal end of the distal shaft is connected to the distal hub and the distal end of the distal shaft is connected the catheter tip; a bifurcated balloon assembly comprising a first balloon and a second balloon, wherein the first balloon and the second balloon are arranged substantially in parallel, and wherein the proximal end of the first balloon is connected to the proximal balloon hub, the distal end of the first balloon is connected to the distal balloon hub, and the distal end of the second balloon is connected to the distal balloon hub.

In another embodiment, a method of deploying a balloon-expandable bifurcated stent into the aorto-iliac bifurcation is disclosed. The method utilizes an embodiment of the balloon catheter described above and a bifurcated balloon-expandable stent crimped onto the balloon assembly. The main body of the bifurcated stent is crimped onto the distal sections of both balloons. The first branch stent of the bifurcated stent is crimped onto the proximal section of the first balloon and the second branch stent of the bifurcated stent is crimped onto the proximal section of the second balloon. The method is comprised of the following steps:

a) Advancing a guidewire from an ipsilateral leg artery through the ipsilateral iliac artery into the aorta.

b) Advancing the balloon catheter over the guidewire until the balloon assembly is distal to the aorto-iliac bifurcation.

c) Advancing the contralateral actuator handle distally to release the tip of the contralateral guidewire from the multi-purpose lumen.

d) Ejecting contrast medium through the multi-purpose lumen to visualize the aorto-iliac bifurcation under fluoroscopy.

e) Advancing the contralateral actuator handle proximally to advance the contralateral guidewire tip into the contralateral iliac artery.

f) Advancing the balloon catheter proximally to place the bifurcated stent onto the aorto-iliac bifurcation.

g) Injecting fluid into the inflation lumen, inflating the balloon assembly, and deploying the bifurcated stent into the aorto-iliac bifurcation.

h) Withdrawing the fluid from the inflation lumen to deflate the balloon assembly.

i) Advancing the balloon catheter distally until the balloon assembly is distal to the aortoiliac bifurcation.

j) Ejecting contrast medium through the multi-purpose lumen to visualize the aorto-iliac bifurcation under fluoroscopy.

k) Retracting the contralateral guidewire into the contralateral balloon shaft.

l) Pulling on the tether wire to place the contralateral balloon parallel to the ipsilateral balloon.

m) Removing the balloon catheter from the patient's body.

The preceding steps do not need to occur in the order presented. Also, in some embodiments not all the steps need to be performed, e.g. steps can be removed. In other embodiments, additional steps can be performed, e.g. steps can be added.

In yet another embodiment, a method of performing a balloon angioplasty of the aortoiliac bifurcation is disclosed. The method utilizes an embodiment of the balloon catheter described above. The method is comprised of the following steps:

a) Advancing a guidewire from an ipsilateral leg artery through the ipsilateral iliac artery into the aorta.

b) Advancing the balloon catheter over the guidewire until the balloon assembly is distal to the aorto-iliac bifurcation.

c) Advancing the contralateral actuator handle distally to release the tip of the contralateral guidewire from the multi-purpose lumen.

d) Ejecting contrast medium through the multi-purpose lumen to visualize the aorto-iliac bifurcation under fluoroscopy.

e) Advancing the contralateral actuator handle proximally to advance the contralateral guidewire tip into the contralateral iliac artery.

f) Advancing the balloon catheter proximally to, at least partially, place the balloon assembly into the branch vessels.

g) Injecting fluid into the inflation lumen, inflating the balloon assembly.

h) Withdrawing the fluid from the inflation lumen to deflate the balloon assembly.

i) Advancing the balloon catheter distally until the balloon assembly is distal to the aortoiliac bifurcation.

j) Ejecting contrast medium through the multi-purpose lumen to visualize the aorto-iliac bifurcation under fluoroscopy.

k) Retracting the contralateral guidewire into the contralateral balloon shaft.

l) Advancing a snare though the multi-purpose lumen.

m) Capturing the contralateral guidewire tip with the snare and pulling the contralateral guidewire tip against or into the proximal balloon hub.

n) Removing the balloon catheter from the patient's body.

The preceding steps do not need to occur in the order presented. Also, in some embodiments not all the steps need to be performed, e.g. steps can be removed. In other embodiments, additional steps can be performed, e.g. steps can be added.

DETAILED DESCRIPTION

Figure 1A:
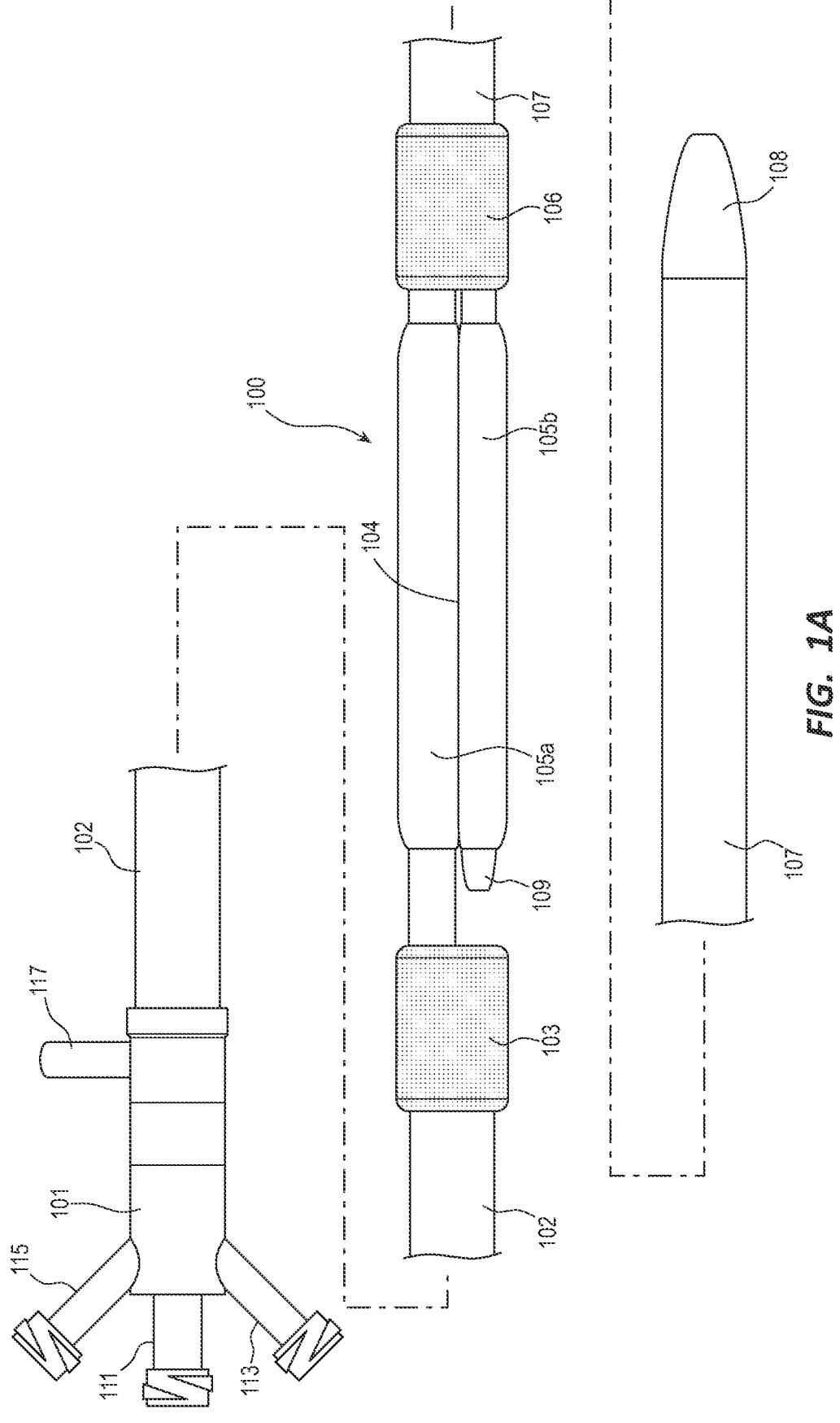
FIG. 1A illustrates an exemplary embodiment of a balloon catheter described herein.
Figure 1B:
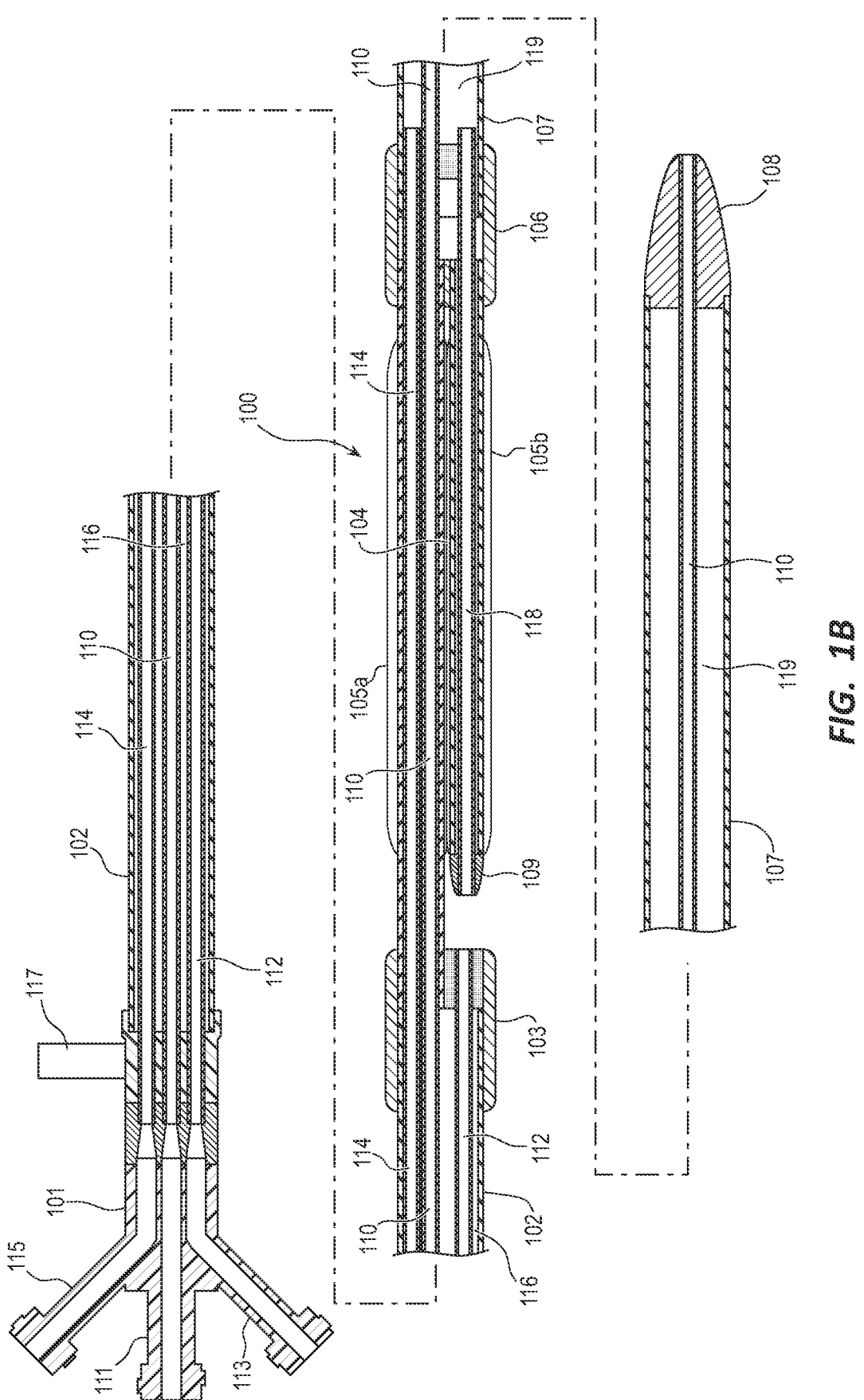
FIG. 1B illustrates a cross-sectional schematic view of the balloon catheter of FIG. 1A.

FIGS. 1A-B illustrate an exemplary embodiment of a balloon catheter. FIG. 1A illustrates the outer components of the balloon catheter. Balloon catheter (100) comprises catheter hub (101) comprising ports (111, 113, 115, 117), proximal shaft (102), proximal balloon hub (103), balloon assembly (104) comprising two balloons (105*a-b*) arranged substantially in parallel, distal balloon hub (106), distal shaft (107), and catheter tip (108). The proximal end of proximal shaft (102) is connected to catheter hub (101) and the distal end of proximal shaft (102) is connected to proximal balloon hub (103). The proximal end of first (ipsilateral) balloon (105*a*) is connected to proximal balloon hub (103) and the distal end of first (ipsilateral) balloon (105*a*) is connected to distal balloon hub (106). The proximal end of second (contralateral) balloon (105*b*) terminates in contralateral tip (109) and the distal end of second (contralateral) balloon (105*b*) is connected to distal balloon hub (106). The proximal end of distal shaft (107) is connected to distal balloon hub (106) and the distal end of distal shaft (107) is connected to catheter tip (108).

FIG. 1B illustrates a cross-sectional schematic of the balloon catheter (100) illustrating the lumens within the balloon catheter (100). First lumen (110) extends from first port (111) to catheter tip (108). Second lumen (112) extends from second port (113) to proximal balloon hub (103). Third lumen (114) extends from third port (115) to distal balloon hub (106). Fourth lumen (116) extends from fourth port (117) to proximal balloon hub (103). Fourth lumen (116) is in fluid communication with first balloon (105*a*) and second balloon (105*b*). Fourth lumen (116) is formed by proximal shaft (102). Fifth lumen (118) extends from contralateral tip (109) to distal balloon hub (106). Sixth lumen (119) extends from distal balloon hub (106) to catheter tip (108). Sixth lumen (119) is formed by distal shaft (107).

In some embodiments, there can be 1, 2, 3, 4, 5, 6, 7, 8, 9, 10 or more lumens within the balloon catheter.

For ease and clarity of disclosure, the lumens in FIG. 1B are illustrated as if the lumens of the catheter were laid out flat and vertically separated from each other with the third lumen (114) above the first lumen (110). This schematic representation is not meant to suggest that in all embodiments the individual lumens would be in the relative positions shown in the schematic view. For example, in some embodiments, each individual internal lumen may comprise a tubular member, where a plurality of these inner tubular members are bundled together within an outer sheath. In such embodiments, the inner bundled tubular members could cross or wrap around each other along the length of the outer sheath. Similarly, other drawings herein indicated as depicting schematic views devices or portions of device within the scope of this disclosure, should also be understood broadly such that the elements of the drawings are not limited to the relative positions shown in the schematic representations.

Figure 2:
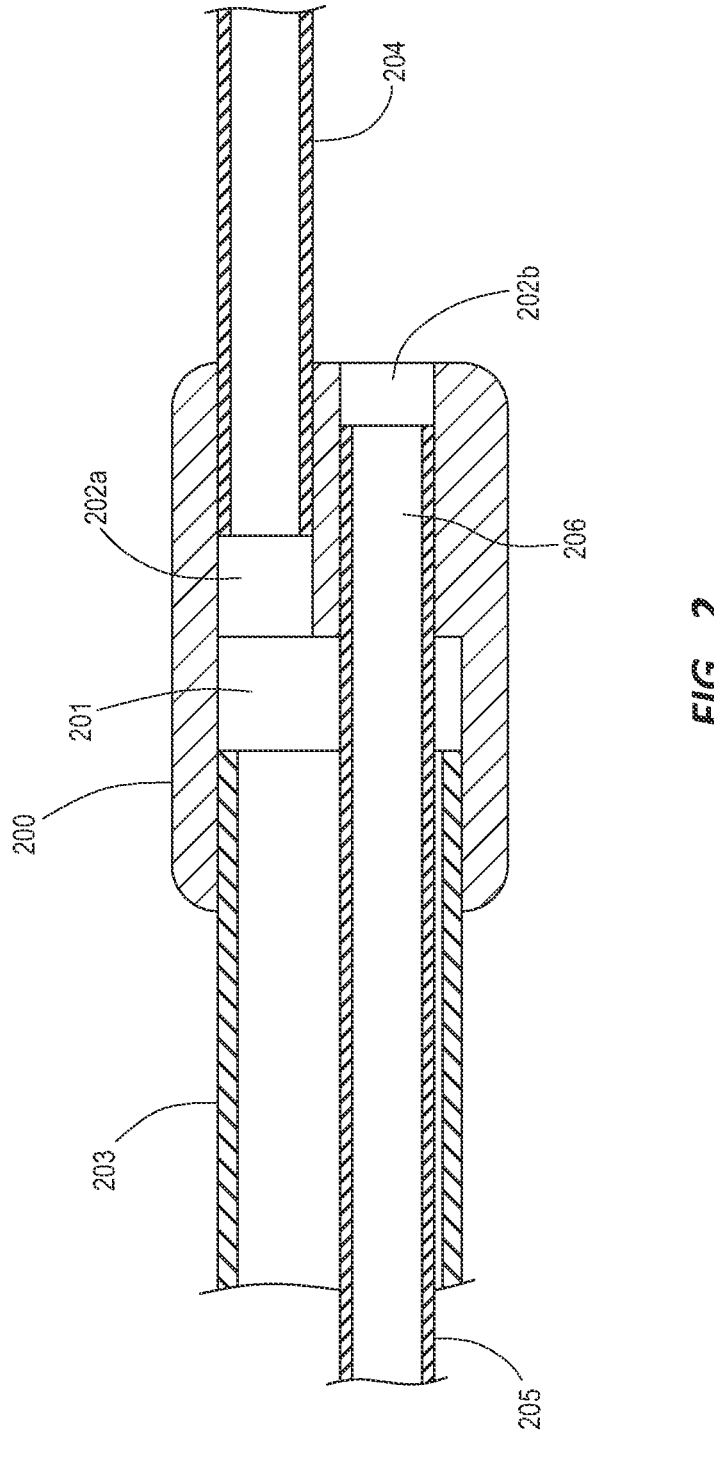
FIG. 2 illustrates an exemplary embodiment of a proximal hub described herein.

FIG. 2 illustrates the lumens terminating in proximal balloon hub (200). Proximal balloon hub (200) comprises one proximal opening (201) and two distal openings (202*a-b*). Proximal shaft (203) is bonded to proximal opening (201). The proximal end of first balloon (204) is bonded into first distal opening (202*a*). The distal end of tubing (205) include second lumen (206) is bonded to second distal opening (202*b*).

In some embodiments, the proximal balloon hub can comprise two proximal openings and one distal opening. In other embodiments, the proximal balloon hub can comprise at least one proximal opening and at least one distal opening. In some embodiments, the proximal balloon hub can comprise one or more proximal openings and one or more distal openings.

Figure 3A:
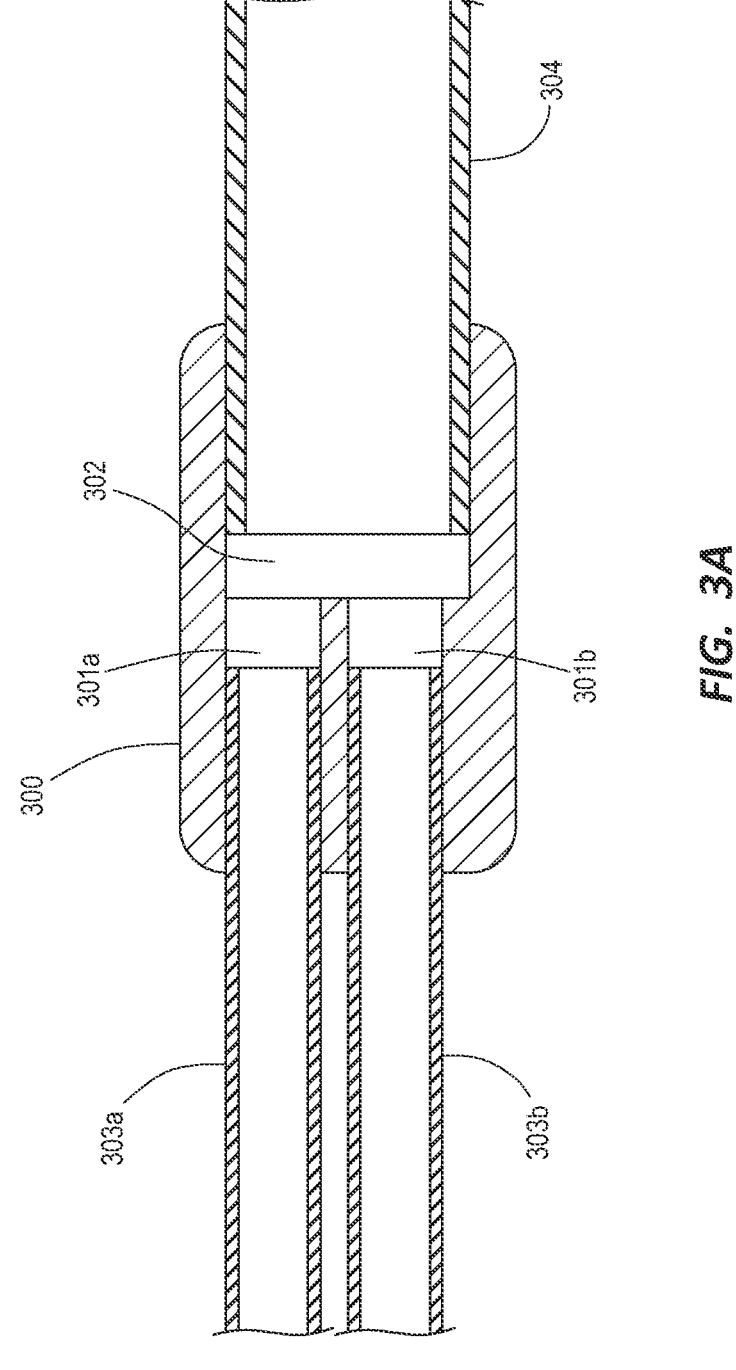
FIG. 3A illustrates a cross-sectional schematic view of an exemplary embodiment of a distal hub described herein.
Figure 3B:
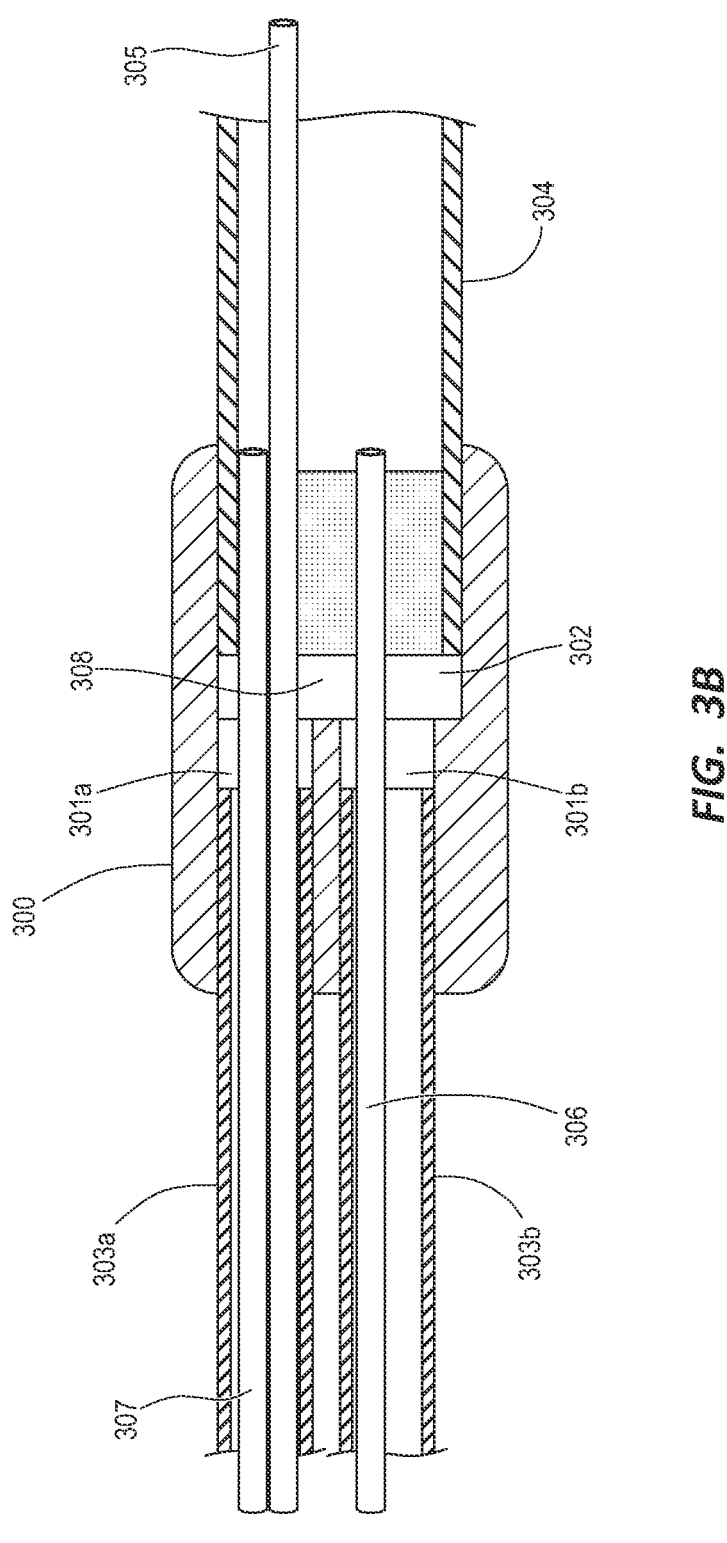
FIG. 3B illustrates a cross-sectional schematic view of lumens in relation to the distal hub of FIG. 3A.

FIGS. 3A-B illustrate a cross-sectional schematic of lumens terminating in distal balloon hub (300). Distal balloon hub (300) comprises two proximal openings (301*a-b*) and one distal opening (302) as shown in FIG. 3A. The distal end of first balloon (303*a*) is bonded to first proximal opening (301*a*) and the distal end of second balloon (303*b*) is bonded to second distal opening (301*b*). The proximal end of distal shaft (304) is bonded to distal opening (302). FIG. 3B illustrates the three additional lumens that pass into or through distal balloon hub (300): first lumen (305), third lumen (306), and fifth lumen (307). The proximal end of distal shaft (304) is sealed off to prevent fluid from first balloon (303*a*) or second balloon (303*b*) from entering the other lumens. Cavity (308) within distal balloon hub (300) provides fluid communication between first balloon (303*a*) and second balloon (303*b*).

In some embodiments, the proximal balloon hub can comprise one proximal opening and two distal openings. In other embodiments, the proximal balloon hub can comprise at least one proximal opening and at least one distal opening. In some embodiments, the proximal balloon hub can comprise one or more proximal openings and one or more distal openings.

In some embodiments, the balloon catheter can comprise three hubs: a catheter hub located at the proximal end of the catheter and two balloon hubs located at the proximal and distal ends of the balloons. At least three lumens terminate at each of the three hubs. The first, second, third, and fourth lumen terminate at the catheter hub. The second and fourth lumen and the lumen of the first balloon terminate at the proximal balloon hub. The third, fifth, and sixth lumen and the lumen of the first balloon and the lumen of the second balloon terminate at the distal balloon hub.

In other embodiments, the balloon catheter can comprise 1, 2, 3, 4, 5, 6 or more hubs.

Figure 4:
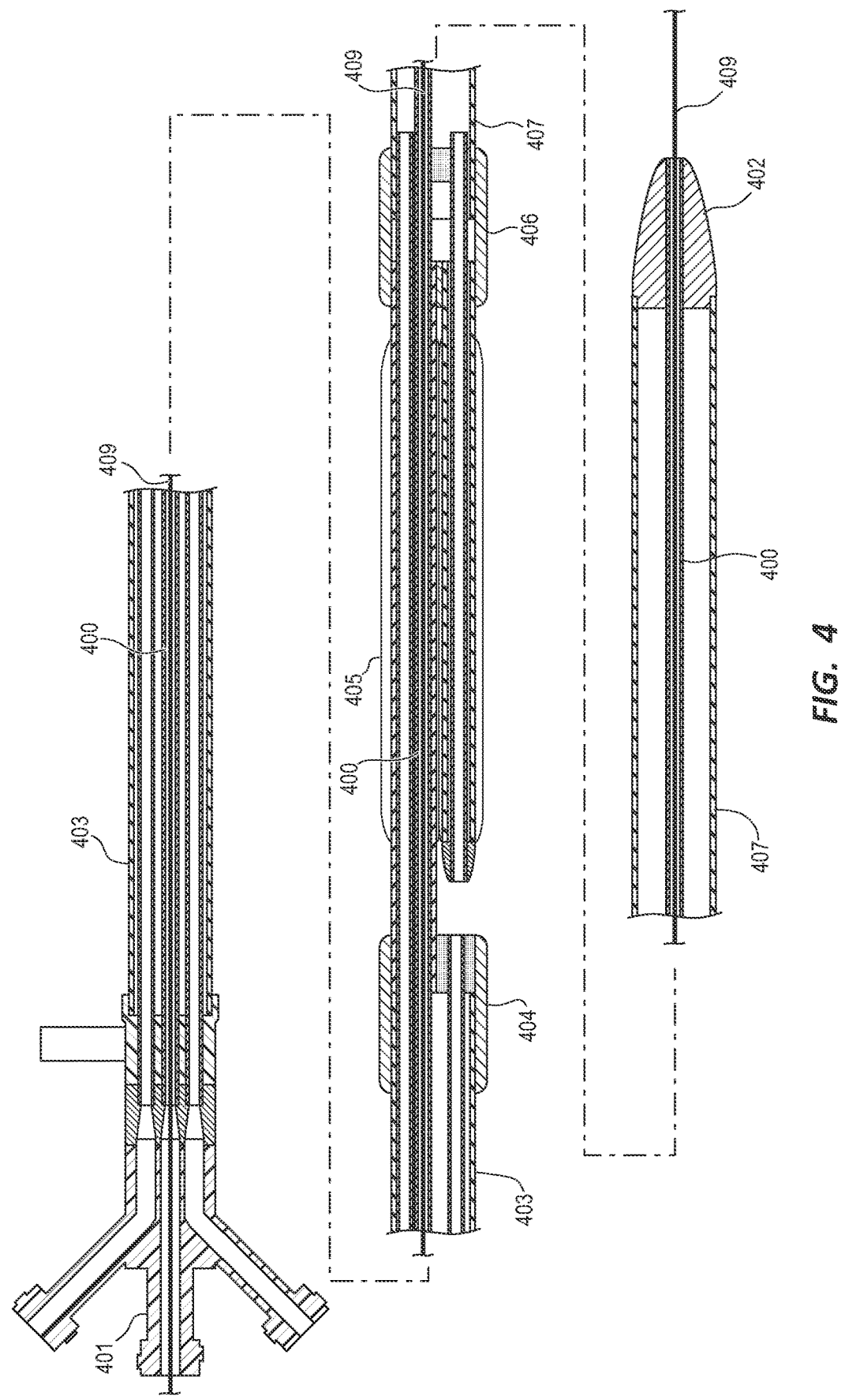
FIG. 4 illustrates a cross-sectional schematic view of a pathway of the aortic guidewire lumen.

FIG. 4 illustrates a cross-sectional schematic view of a function of first lumen (400). First lumen (400) extends from first port (aortic guidewire port) (401) to catheter tip (402). It passes through proximal shaft (403), proximal balloon hub (404), first balloon (405), distal balloon hub (406), distal shaft (407), and catheter tip (408). It provides a passage for guidewire (aortic guidewire) (409) over which the balloon catheter may be advanced into the aorta.

Figure 5:
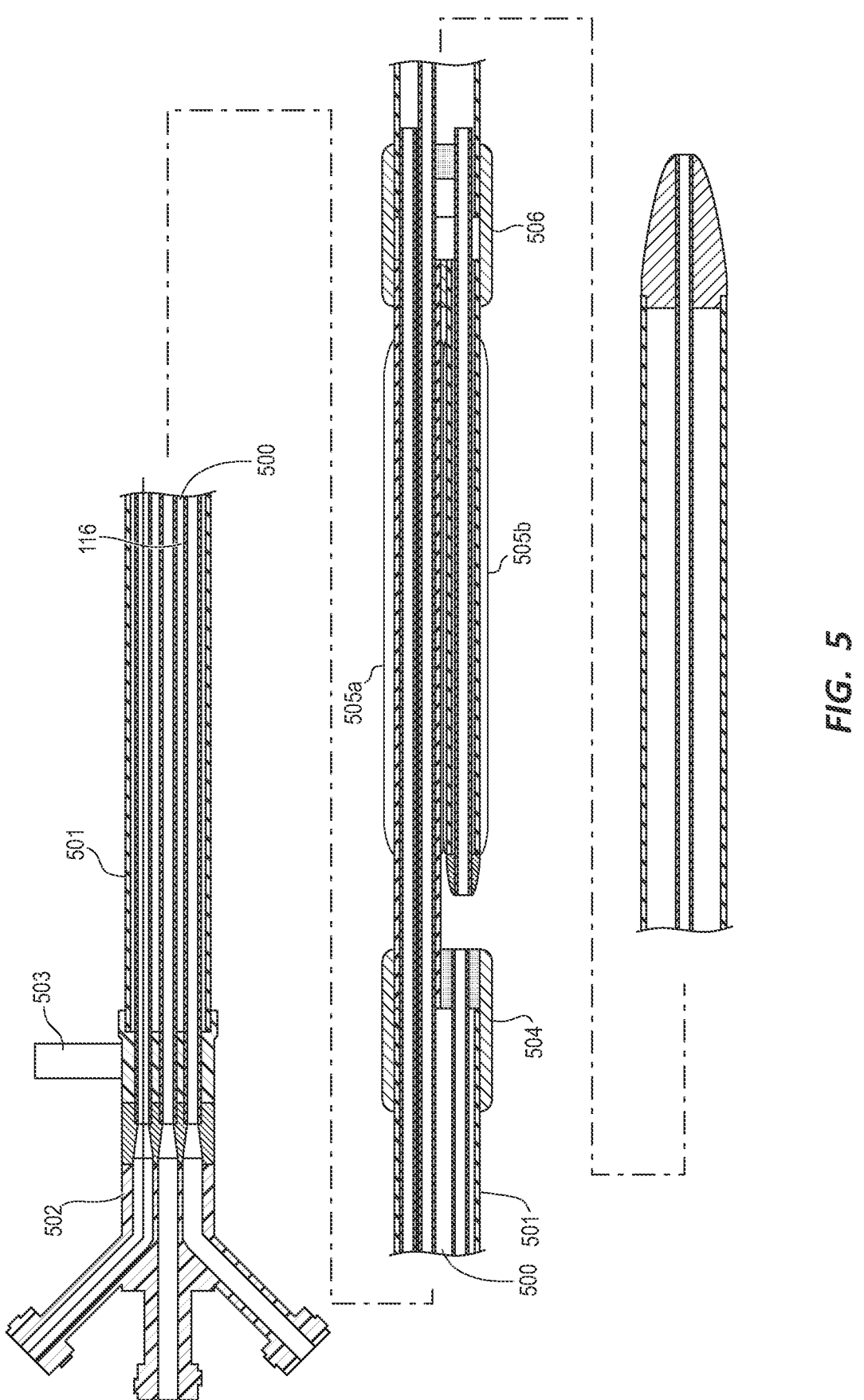
FIG. 5 illustrates a cross-sectional schematic view of a pathway of the inflation lumen.

FIG. 5 illustrates a cross-sectional schematic view of a function of fourth lumen (500). Fourth lumen (500) is formed by proximal shaft (501) and catheter hub (502). Fourth lumen (500) extends from fourth port (inflation port) (503) in catheter hub (502) to proximal balloon hub (504). Fourth lumen (500) is sealed off on the proximal end to prevent fluid from entering the proximal section of the catheter hub (502). Fourth lumen (500) is in fluid communication with the balloon (505*a*), cavity (506), and second balloon (505*b*). Fourth lumen (500), balloons (505*a-b*), and cavity (506) together form a bifurcated inflation lumen. The purpose of the bifurcated inflation lumen is to simultaneously inflate first balloon (505*a*) and second balloon (505*b*) when fluid is injected into inflation port (503).

Figure 6A:
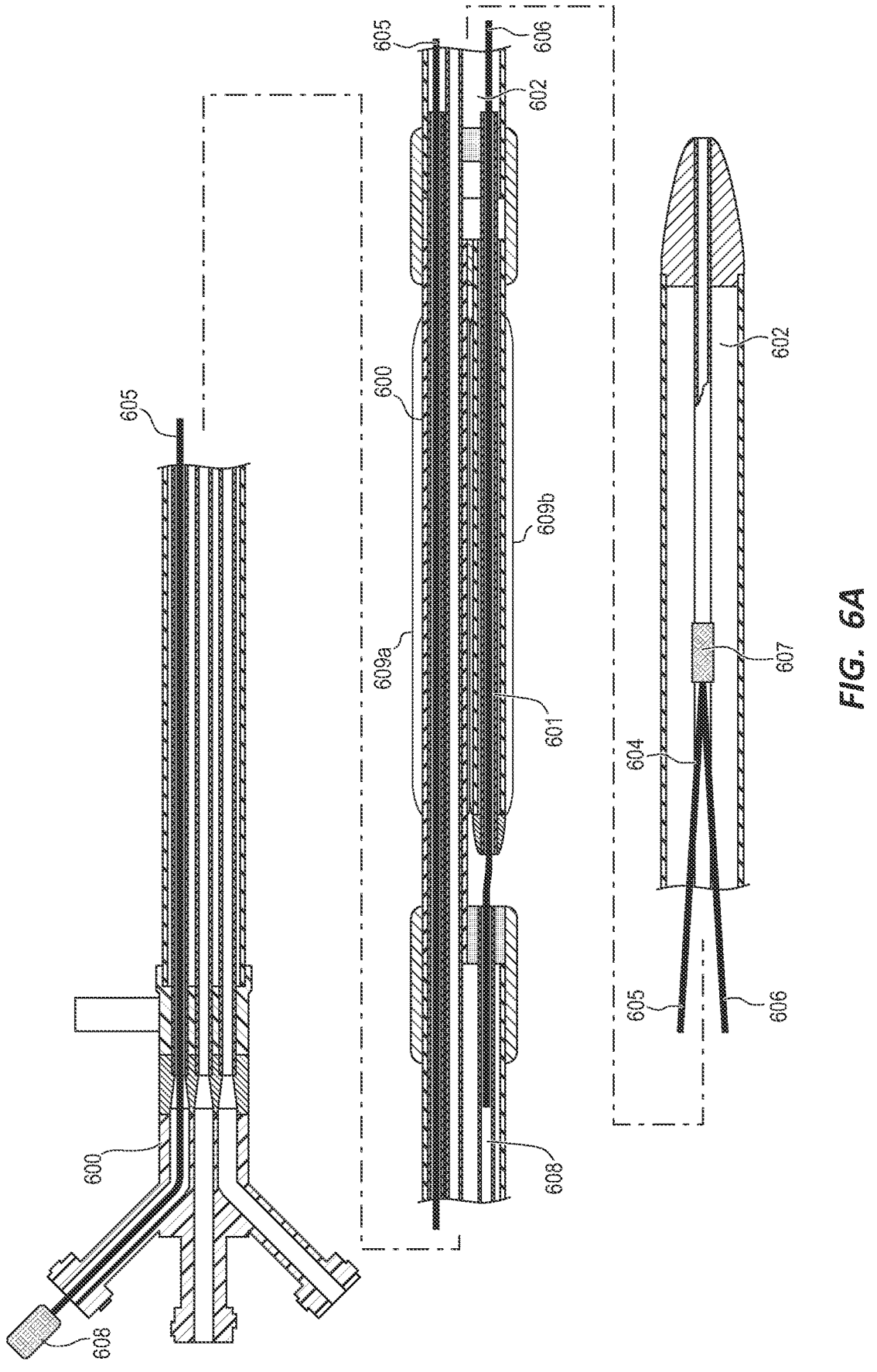
FIG. 6A illustrates a cross-sectional schematic view of a contralateral guidewire assembly describe herein in a first position.
Figure 6B:
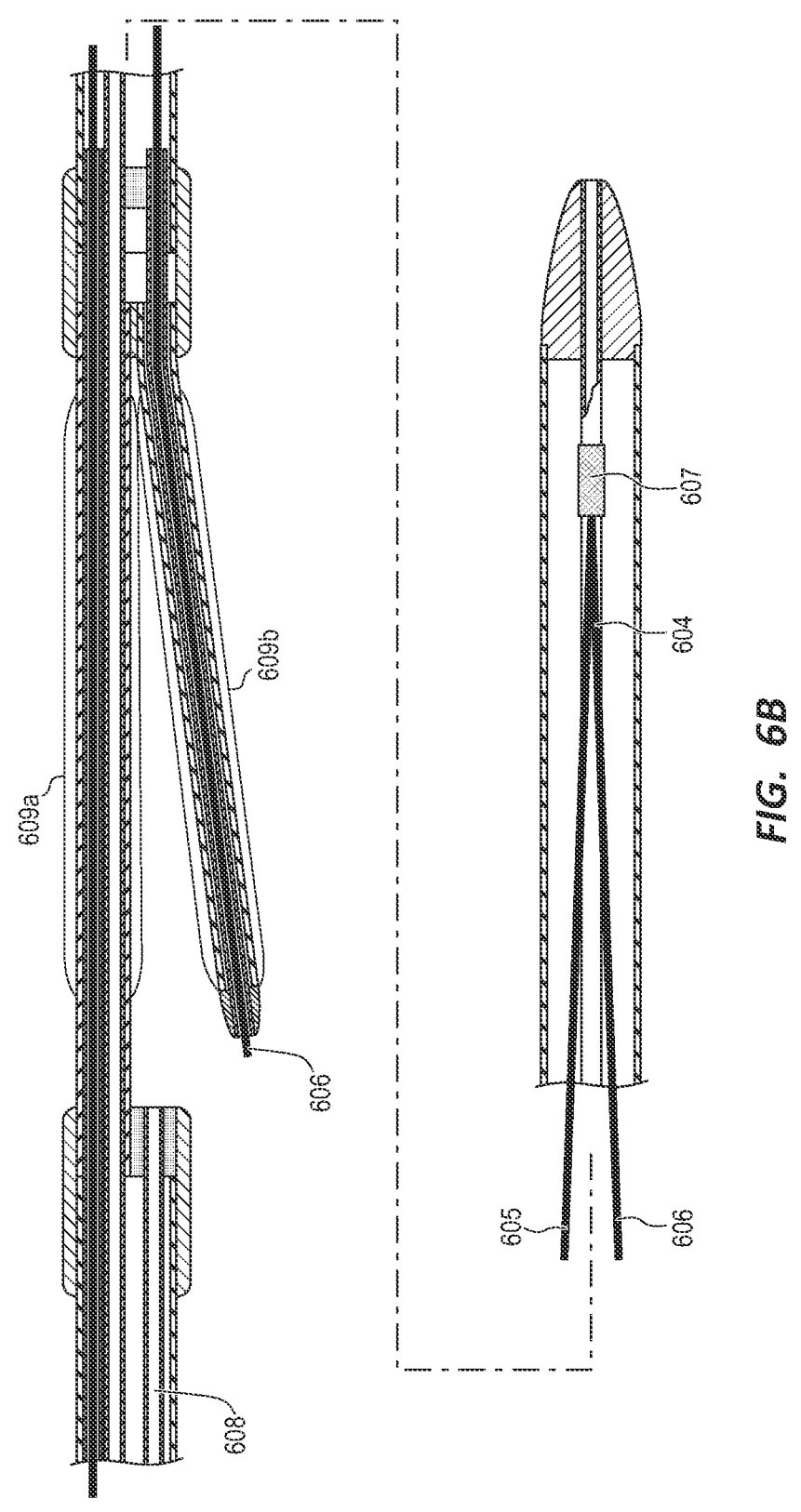
FIG. 6B illustrates the contralateral guidewire assembly of FIG. 6B in a second position.
Figure 6C:
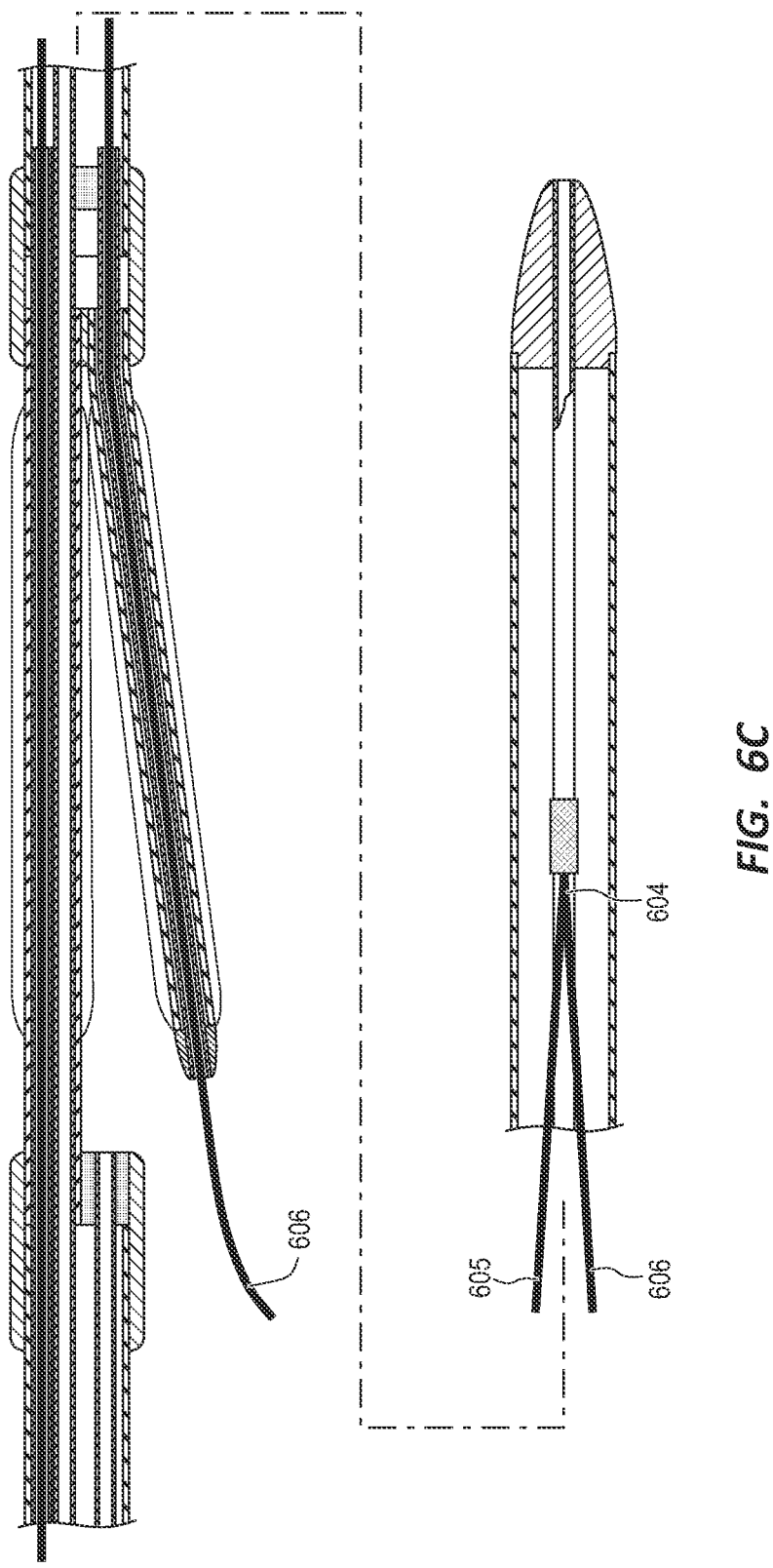
FIG. 6C illustrates the contralateral guidewire assembly of FIG. 6C in a third position.

FIGS. 6A-C illustrate a cross-sectional schematic view of a function of third lumen (600), fifth lumen (601), and sixth lumen (602). Lumens (600, 601, 602) form a bifurcated guidewire lumen. The bifurcated guidewire lumen houses contralateral guidewire assembly (604). Contralateral guidewire assembly (604) comprises of actuator wire (605) that partially resides in third lumen (600), contralateral guidewire (606) that partially resides in fifth lumen (601), and contralateral guidewire connector (607) that is housed within sixth lumen (602). Actuator wire (605) extends from the third lumen (600) to sixth lumen (602). Contralateral guidewire (606) extends from sixth lumen (602), through fifth lumen (601) beyond a contralateral tip of second balloon (609b) and into second lumen (608). Actuator wire (605) and the contralateral guidewire (606) are each coupled to the contralateral guidewire connector (607). Actuator handle (610) is connected to the proximal end of actuator wire (605). FIG. 6A illustrates a first position of contralateral guidewire assembly (604). The proximal end of contralateral guidewire (606) sits inside second lumen (608). In the first position, second balloon (609b) is locked in a parallel configuration to first balloon (609a). In this configuration, the balloon catheter is inserted into the vasculature. FIG. 6B shows a second position of contralateral guidewire assembly (604) after a distal push of the actuator handle (610). Contralateral guidewire assembly (604) is translated distally. The proximal end of contralateral guidewire (606) is released from second lumen (608). In the second position, second balloon (609b) can rotate away from first balloon (609a). In this configuration, contralateral guidewire (606) is positioned for cannulation of a branch vessel. FIG. 6C illustrates contralateral guidewire assembly (604) in a third position after a proximal pull of the actuator handle (610). Contralateral guidewire assembly (604) is translated proximally to advance contralateral guidewire (606) into the branch vessel.

Figure 7A:
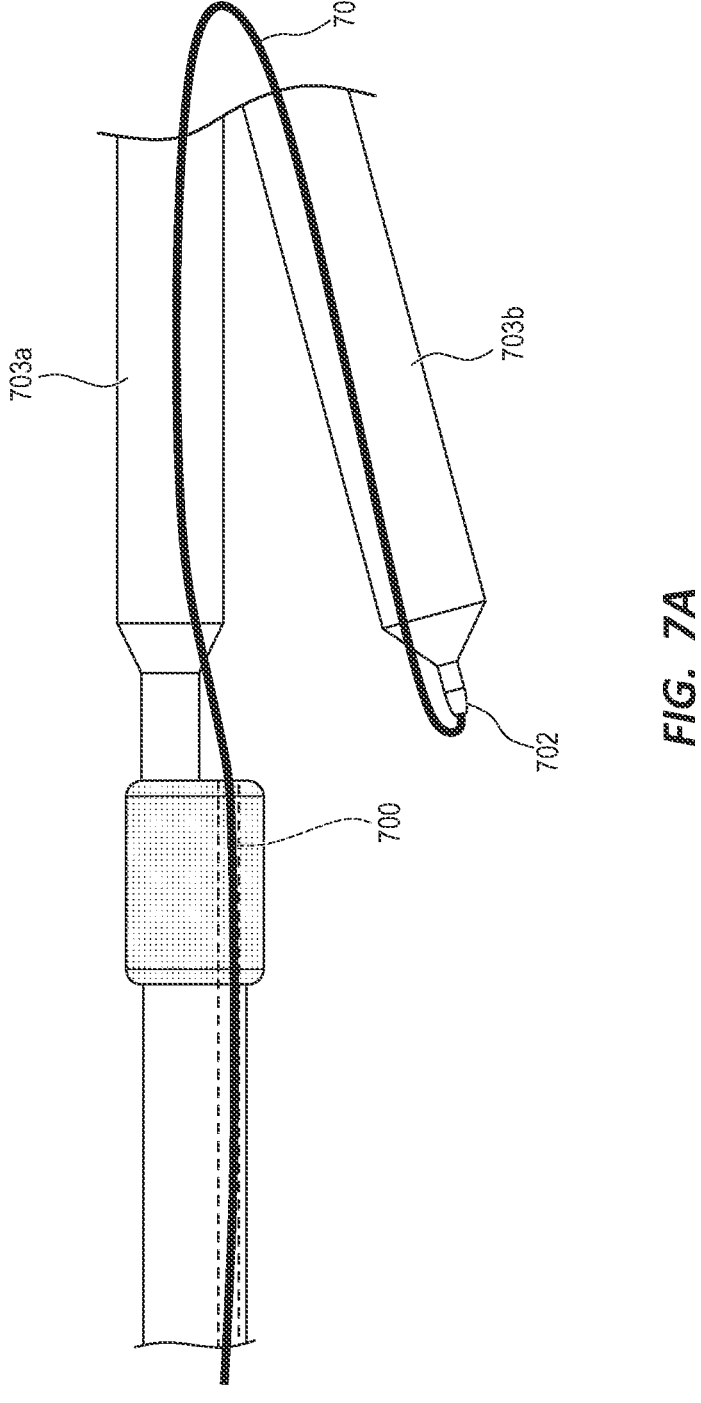
FIG. 7A illustrates an exemplary embodiment of a tether wire described herein.
Figure 7B:
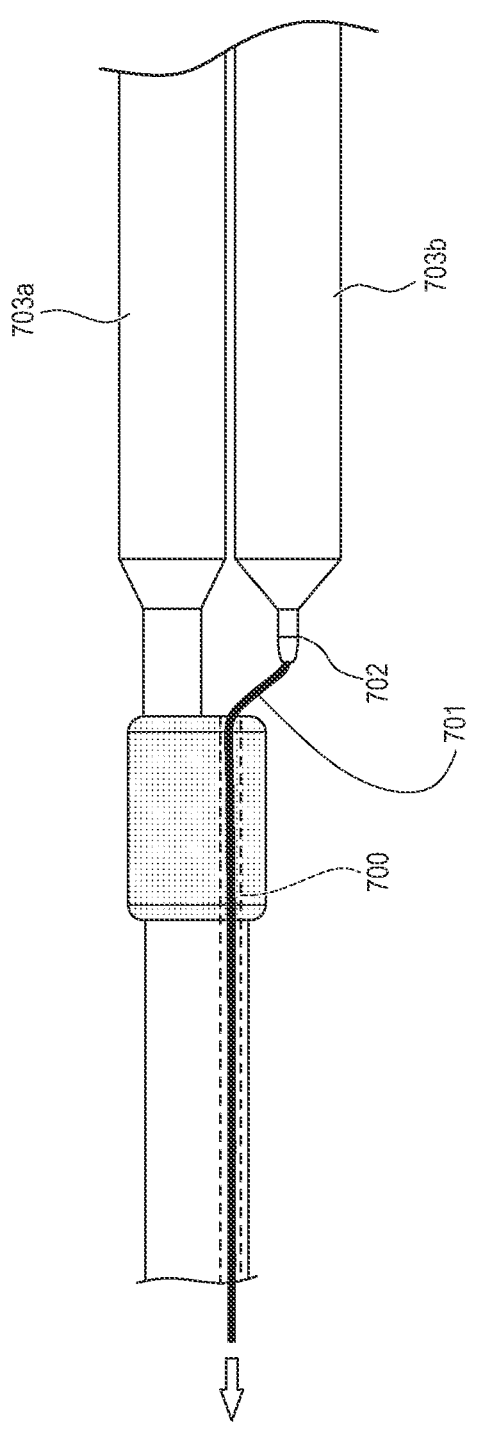
FIG. 7B illustrates the tether wire of FIG. 7A with a first balloon and a second balloon substantially parallel.

FIGS. 7A-B illustrate another function of second lumen (700). Tether wire (701) is connected to contralateral tip (702) and routed through second lumen (700) as illustrated in FIG. 7A. Tether wire (701) exits second lumen (700) at the catheter hub (not shown). Pulling on tether wire (701) pulls second balloon (703b) into a parallel configuration to first balloon (703a) as illustrated in FIG. 7B. In this configuration, the balloon catheter can be retracted from the vasculature. Tether wire (701) can be made from a metal alloy including, but not limited to, stainless steel and Nitinol. Tether wire (701) can be made from polymer or glass fibers including, but not limited to, Kevlar and polyethylene. Tether wire (701) can be made from a braided suture or braided wire.

Figure 8A:
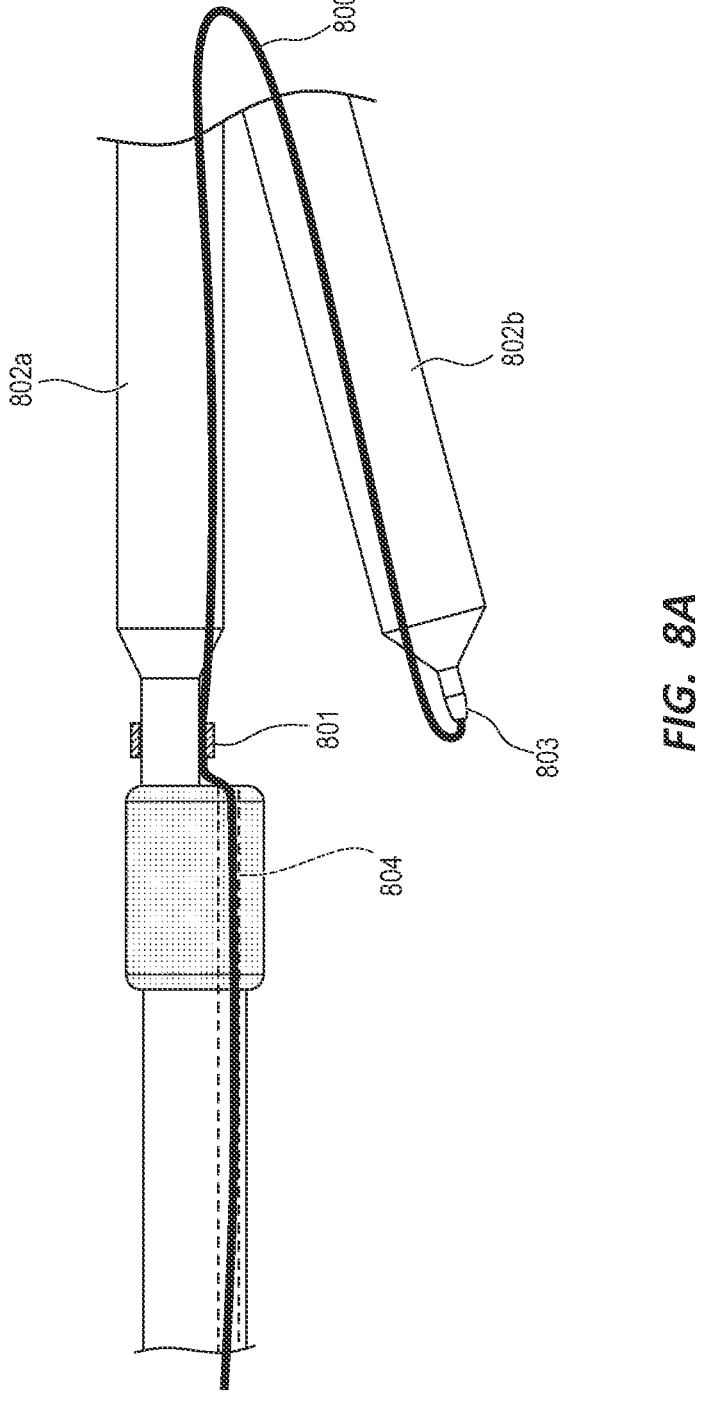
FIG. 8A illustrates an alternative routing path of the exemplary embodiment of the tether wire.
Figure 8B:
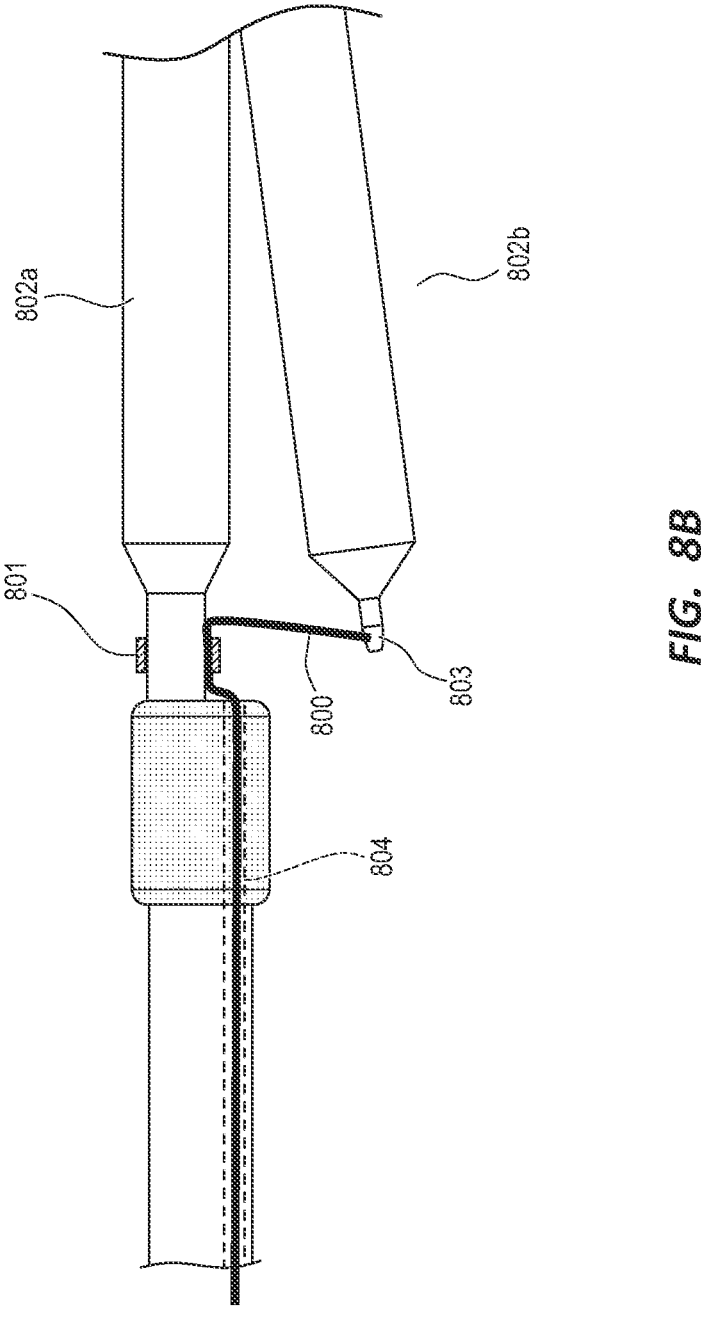
FIG. 8B illustrates the tether wire of FIG. 8A pulling a second balloon toward a first balloon.

FIGS. 8A-B illustrate an alternative pathway of tether wire (800). Loop (801) is attached to a proximal end of first balloon (802a). Loop (801) forms a passageway for tether wire (800). Tether wire (800) is routed from contralateral tip (803) through loop (801) into second lumen (804) as illustrated in FIG. 8A. An advantage of the alternative pathway of tether wire (800) is that the tether forces acting on contralateral tip (803) are directed more perpendicular to the axis of first balloon (802a) as illustrated in FIG. 8B, requiring less force to pull second balloon (802b) against first balloon (802a).

Figure 9A:
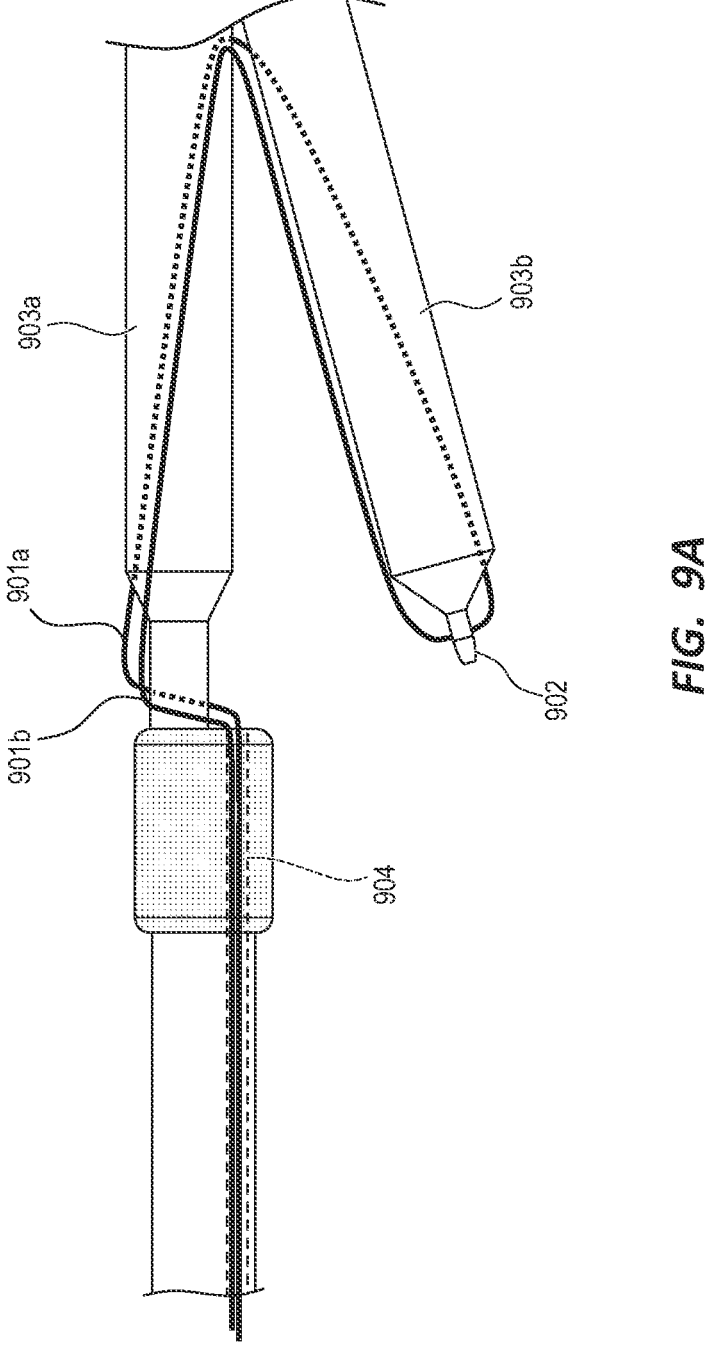
FIG. 9A illustrates an alternative embodiment of a tether wire.
Figure 9B:
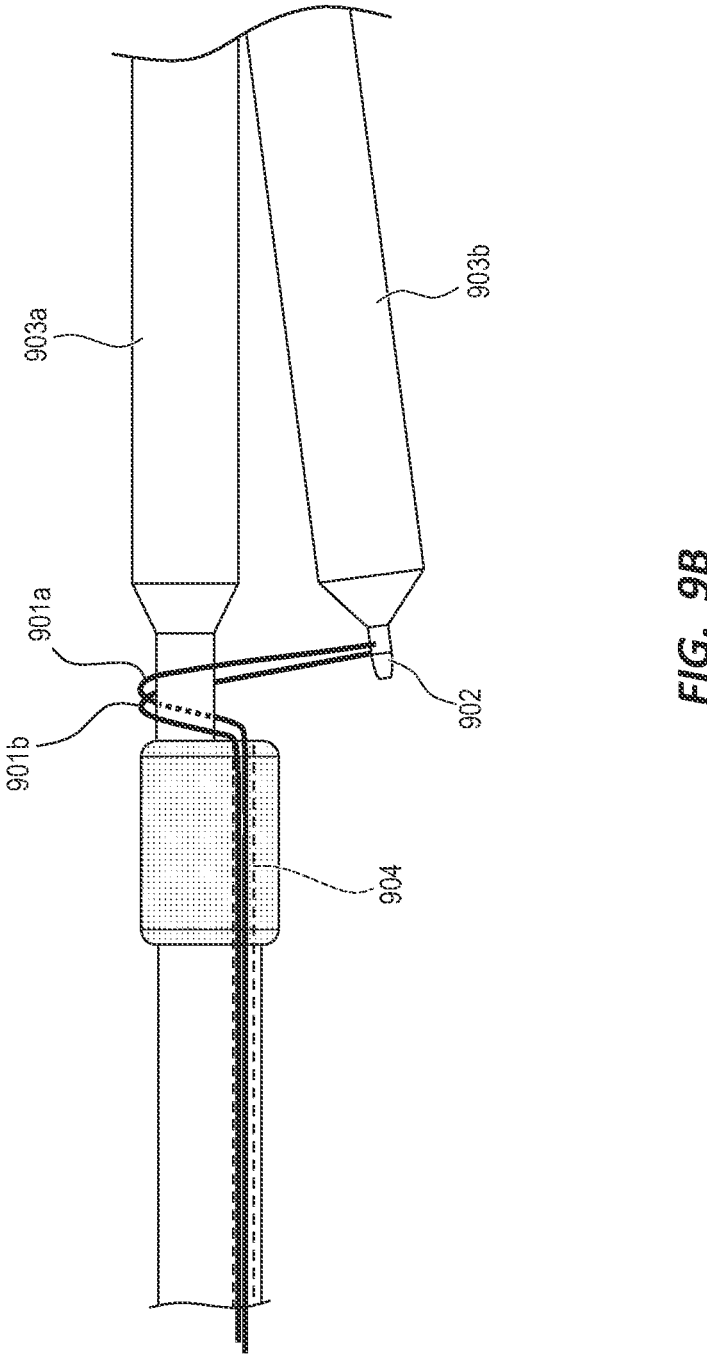
FIG. 9B illustrates the tether wire of FIG. 9A pulling a second balloon toward a first balloon.

FIGS. 9A-B illustrate another embodiment of the tether wire. First tether wire (901a) and second tether wire (901b) are connected to contralateral tip (902). First tether wire (901a) wraps clockwise, and second tether wire (901b) wraps counterclockwise around the tail of first balloon (903a) before entering second lumen (904) as illustrated in FIG. 9A. Simultaneously pulling on first tether wire (901a) and second tether wire (901b) pulls the second balloon (903b) against the first balloon (903a) as illustrated in FIG. 9B.

Besides housing the tether wire, the second lumen can serve other functions. For example, in some embodiments, the second lumen can provide a passage for advancing a snare from the catheter hub. The snare can be used as an alternative way of pulling the second balloon toward the first balloon. The second lumen can also be used for injecting contrast medium into the blood stream. In other embodiments of the balloon catheter, the multi-purpose second lumen can be replaced by more than one lumen(s) that perform the individual functions described herein.

Figure 10:
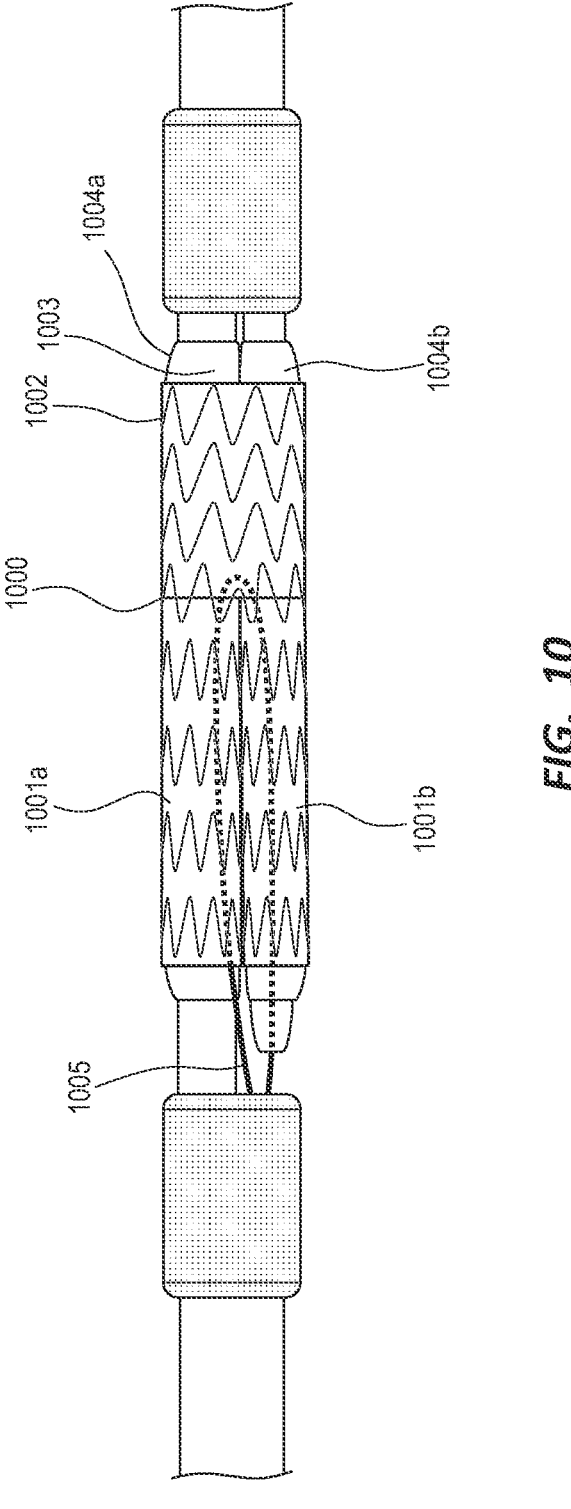
FIG. 10 illustrates a bifurcated stent crimped onto the bifurcated balloon assembly.

FIG. 10 shows covered bifurcated balloon-expandable stent (1000) crimped onto balloon assembly (1003). Covered bifurcated balloon-expandable stent (1000) comprises first branch stent (1001a), second branch stent (1001b), and main body stent (1002). First branch stent (1001a) is crimped onto and disposed around the proximal section of first balloon (1004a). Second branch stent (1001b) is crimped onto and disposed around proximal section of second balloon (1004b). Main body stent (1002) is simultaneously crimped onto and disposed around the distal segments of first balloon (1004a) and second balloon (1004b). Tether wire (1005) is routed through the lumen of covered bifurcated balloon-expandable stent (1000) through the first branch stent (1001a) and curves into the second branch stent (1001b). In some embodiments, the crimping is not simultaneous.

Figure 11:
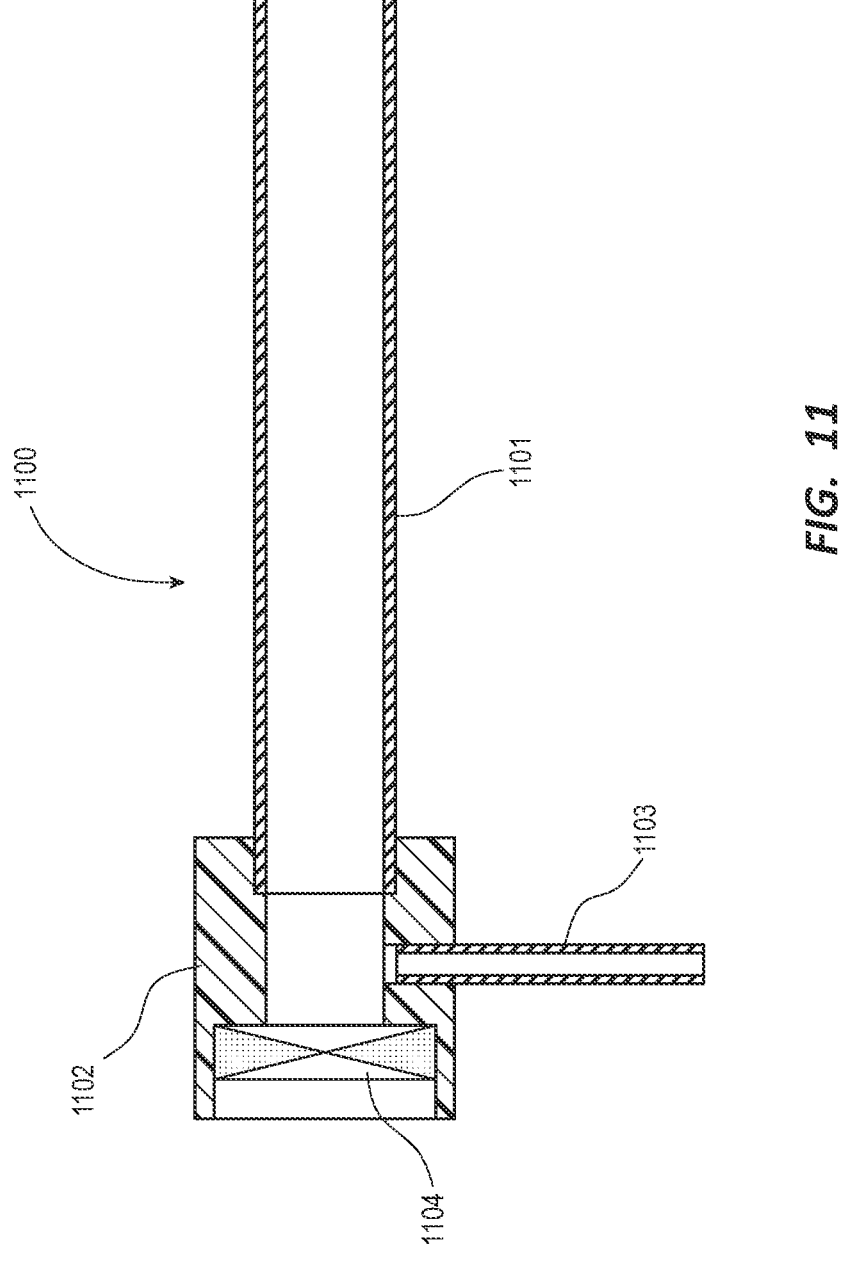
FIG. 11 illustrates a representative introducer sheath.

An introducer sheath can be used to facilitate the insertion of the balloon catheter into the vasculature. FIG. 11 shows representative introducer sheath (1100). Introducer sheath (1100) comprises shaft (1101), hub (1102), side port (1103) connected to hub (1102), and hemostasis valve (1104) placed at the proximal end of hub (1102) to prevent backflow of blood through introducer sheath (1100). Hemostasis valve (1104) can be made from an elastomeric material to allow for passage of guidewires and interventional devices of various sizes.

Figure 12:
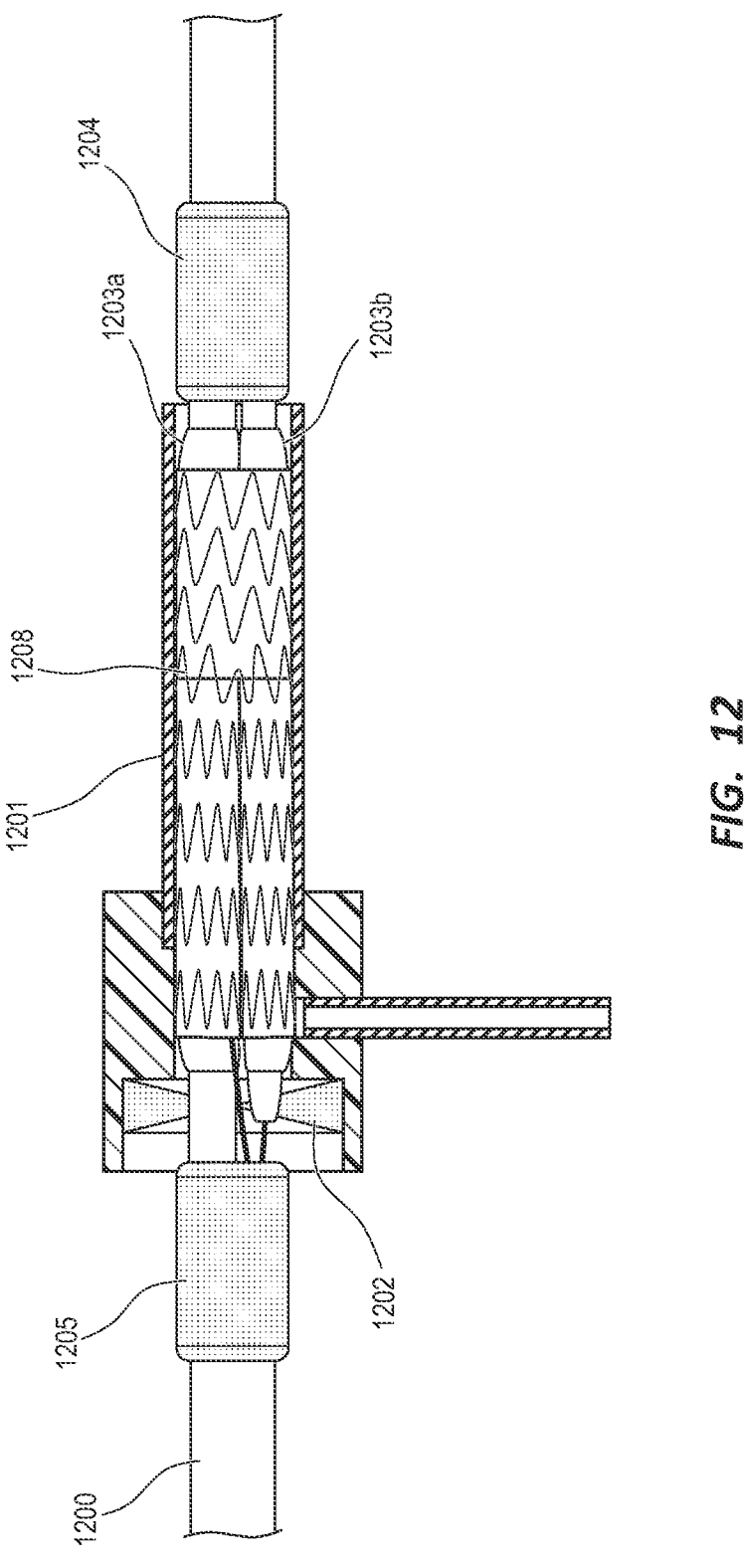
FIG. 12 illustrates the exemplary embodiment of a balloon catheter inserted into the representative introducer sheath.

FIG. 12 illustrates balloon catheter (1200) described herein inserted into introducer sheath (1201). Distal balloon hub (1204) and proximal balloon hub (1205) can have outer diameters close to the inner diameter of introducer sheath (1201) to center balloon catheter (1200) in introducer sheath (1201). This can minimize interference between deflated balloons (1203a-b) and the tip of introducer sheath (1201) during retraction of balloon catheter (1200) into introducer sheath (1201). Hemostasis valve (1202) of introducer sheath (1201) compresses onto balloon catheter (1200) to create a hemostatic seal. As balloon catheter (1200) is advanced through introducer sheath (1201), hemostasis valve (1202) can get caught in the transitions from balloons (1203a-b) to proximal balloon hub (1205) and distal balloon hub (1204). This can increase the forces required to advance or retract balloon catheter (1200). It can also cause damage to hemostasis valve (1202), bifurcated stent (1208), or balloon catheter (1200). To overcome this shortcoming, some embodiments of the present disclosure include a protective sheath to facilitate the passage of the balloon catheter through an introducer sheath.

Figure 13:
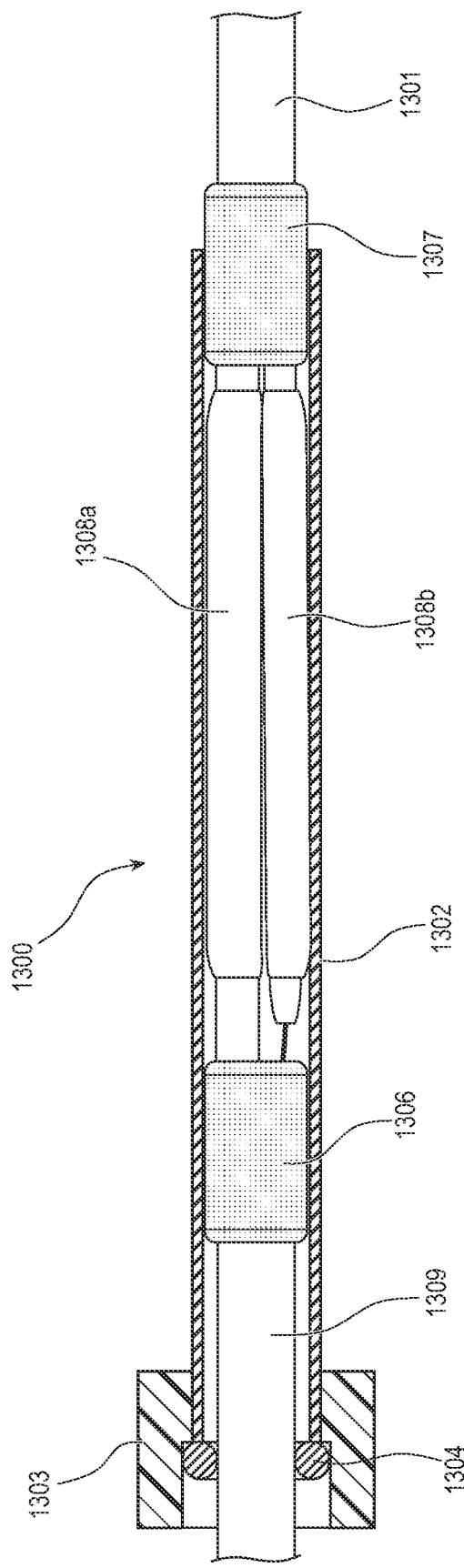
FIG. 13 illustrates a protective sheath mounted onto the exemplary embodiment of a balloon catheter.

FIG. 13 shows an exemplary embodiment of protective sheath (1300) mounted on balloon catheter (1301) of an embodiment of the present disclosure. Protective sheath (1300) comprises shaft (1302), hub (1303), and sealing member (1304) placed at the proximal end of hub (1303). Sealing member (1304) is designed to prevent backflow of blood through protective sheath (1300). In some embodiments (not shown), a side port can be connected to hub (1303) for flushing the lumen of protective sheath (1300). In other embodiments, the second lumen of balloon catheter (1301) that terminates at proximal balloon hub (1306) can be used to flush protective sheath (1300). Protective sheath (1300) extends from proximal balloon hub (1306) to distal balloon hub (1307) and covers first balloon (1308a) and second balloon (1308b). Sealing member (1304) seals hub (1303) against proximal shaft (1309).

Figure 14A:
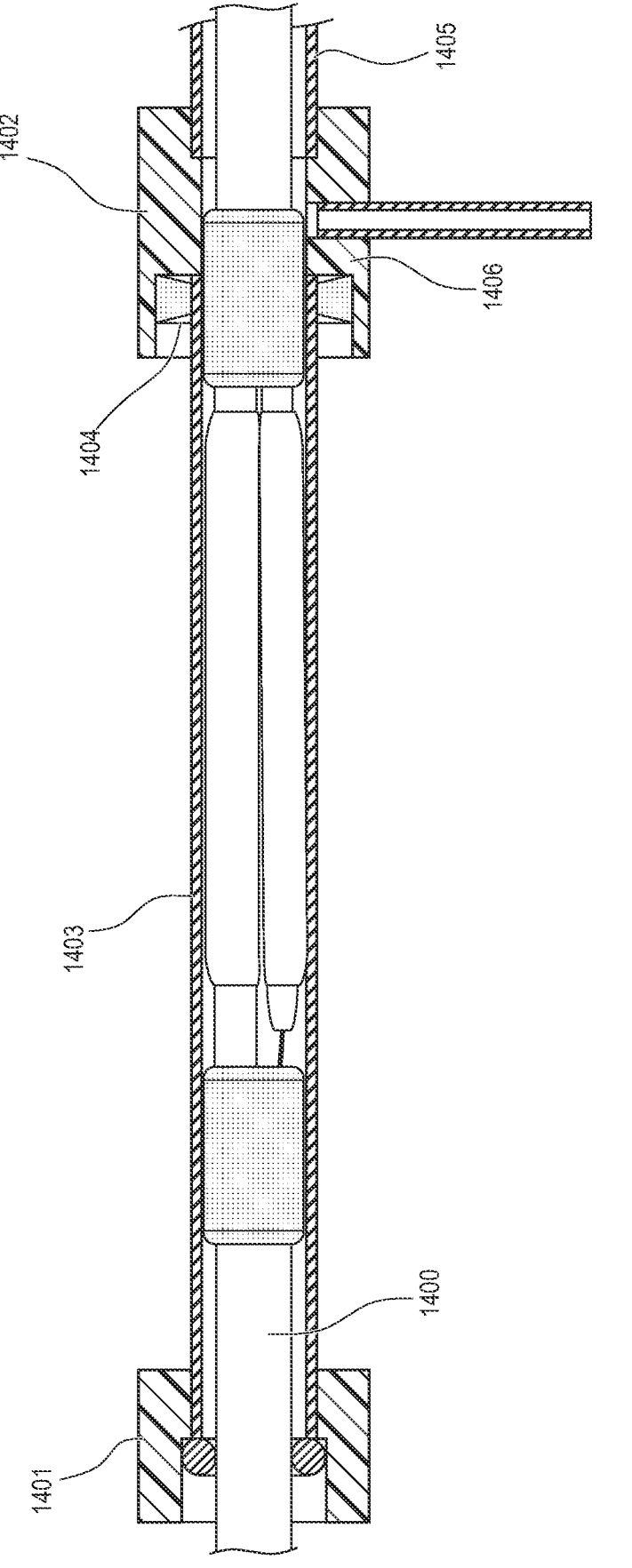
FIG. 14A illustrates an exemplary embodiment of a balloon catheter containing a protective sheath inserted into a representative introducer sheath.
Figure 14B:
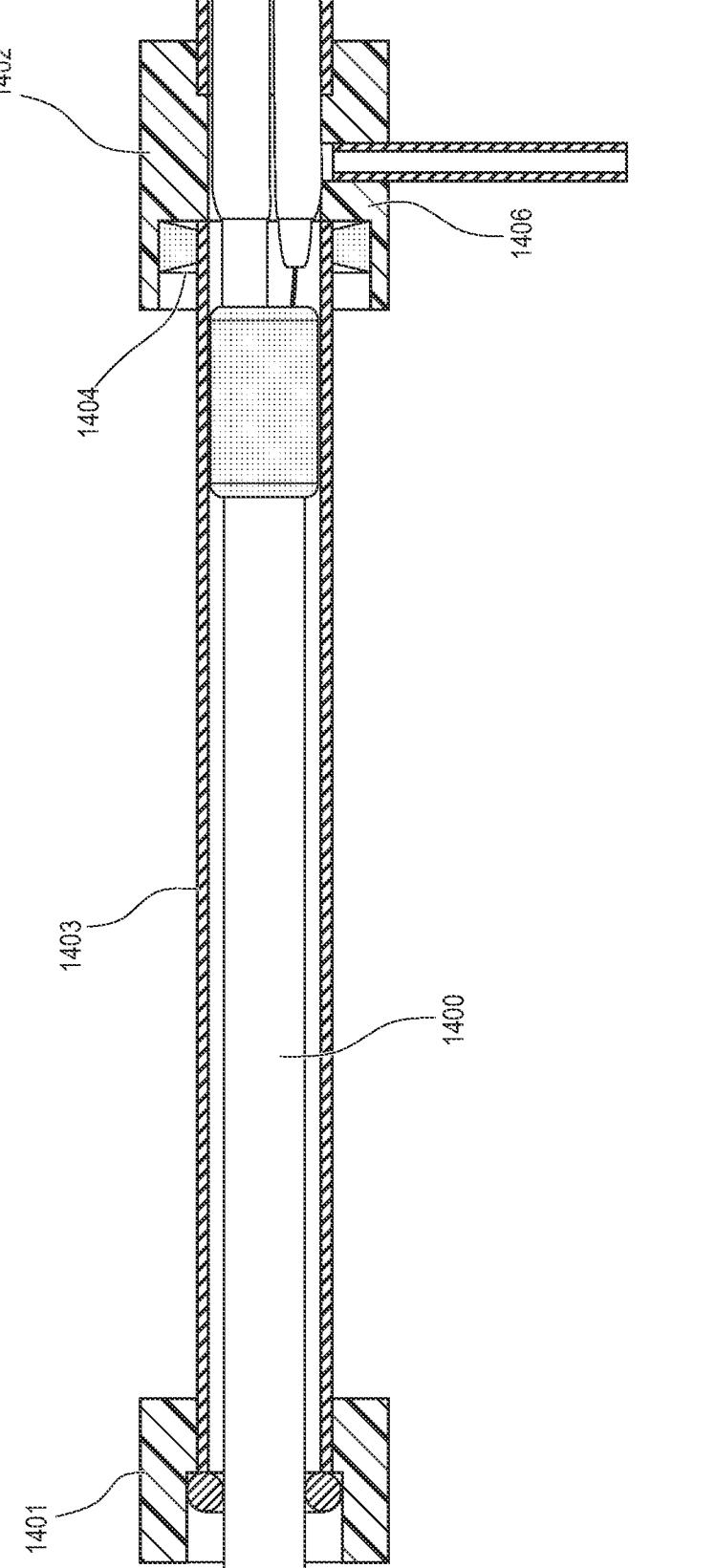
FIG. 14B illustrates the balloon catheter of FIG. 14A being advance through the protective sheath.

FIGS. 14A-B show balloon catheter (1400) with protective sheath (1401) inserted into introducer sheath (1402). Shaft (1403) of protective sheath (1401) is passed through hemostasis valve (1404). The inner diameter of protective sheath (1401) can be close to or identical to the inner diameter of introducer sheath (1402). Shaft (1403) of protective sheath (1401) and shaft (1405) of introducer sheath (1402) form a continuous unobstructed passageway for the balloon catheter (1400). FIG. 14A shows protective sheath (1401) fully inserted into hub (1406) of introducer sheath (1402). FIG. 14B shows balloon catheter (1400) being advanced through shaft (1403) of protective sheath (1401) and shaft (1405) of introducer sheath (1402). Shaft (1403) of protective sheath (1401) prevents interference between hemostasis valve (1404) and balloon catheter (1400).

Figure 15A:
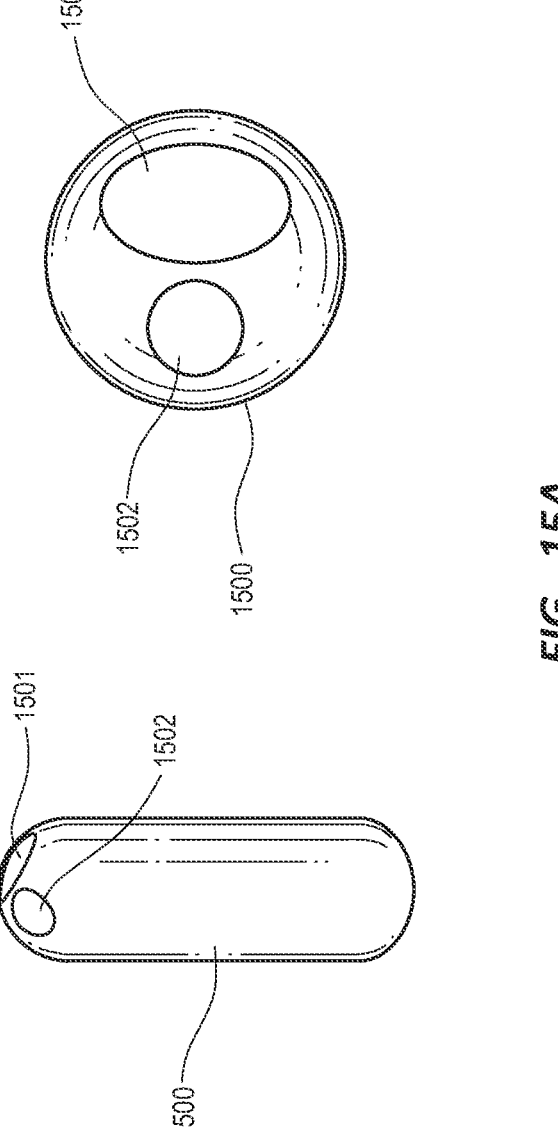
FIG. 15A illustrates a perspective view of an exemplary embodiment of a proximal balloon hub.
Figure 15B:
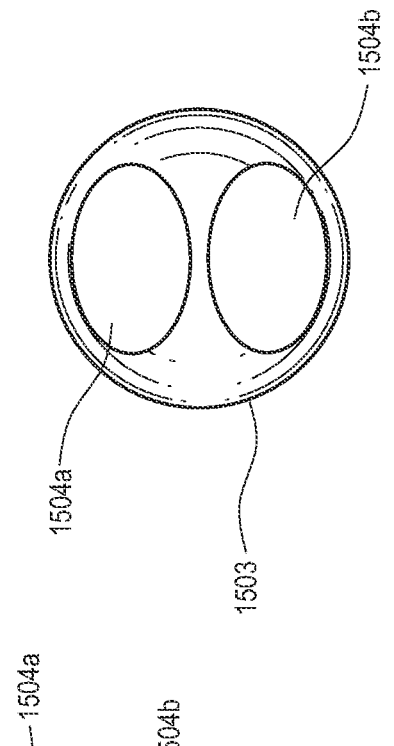
FIG. 15B illustrates a perspective view of an exemplary embodiment of a distal balloon hub.
Figure 15B:
Figure 15C:
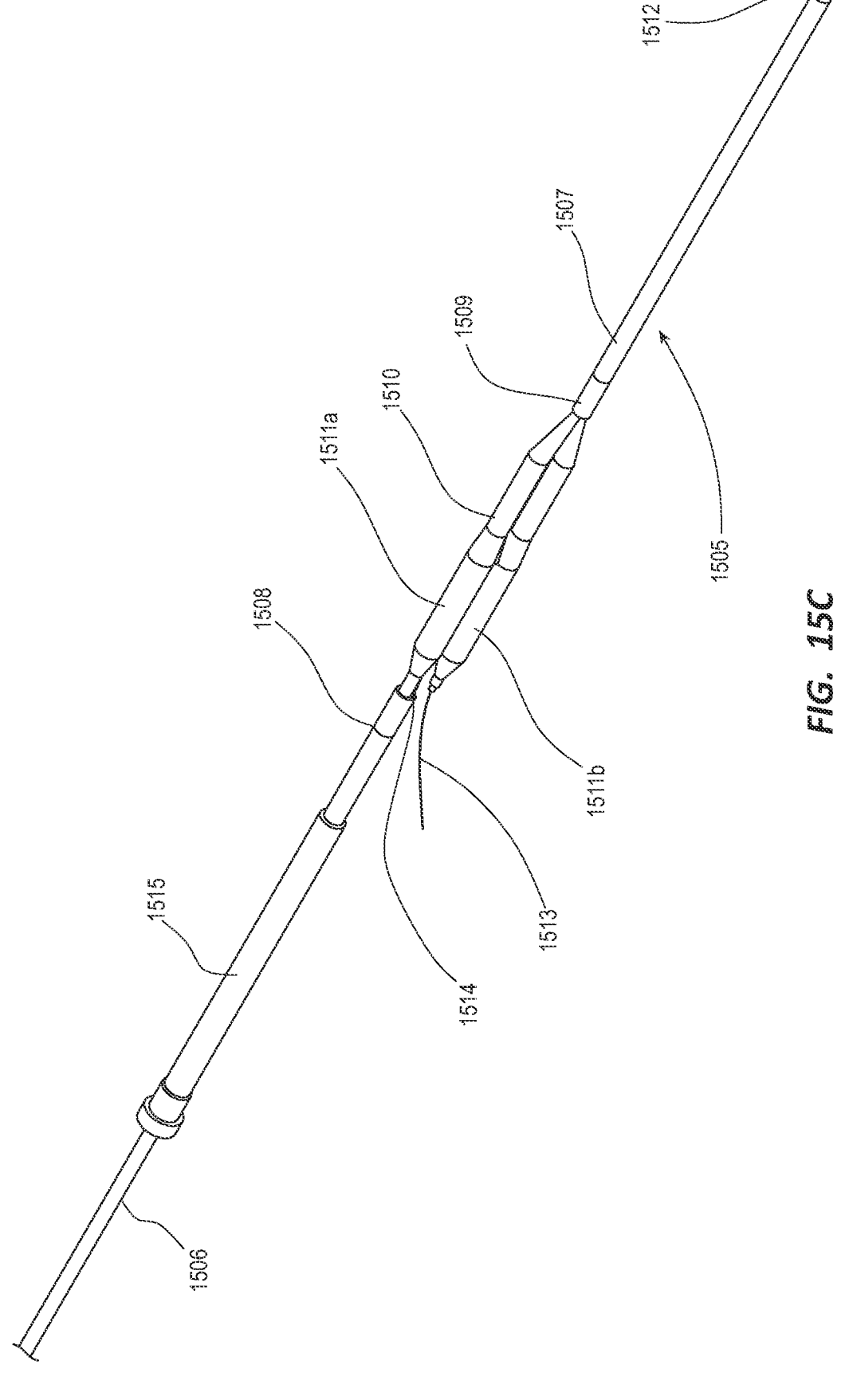
FIG. 15C illustrates a perspective view of balloon catheter.
Figure 15D:
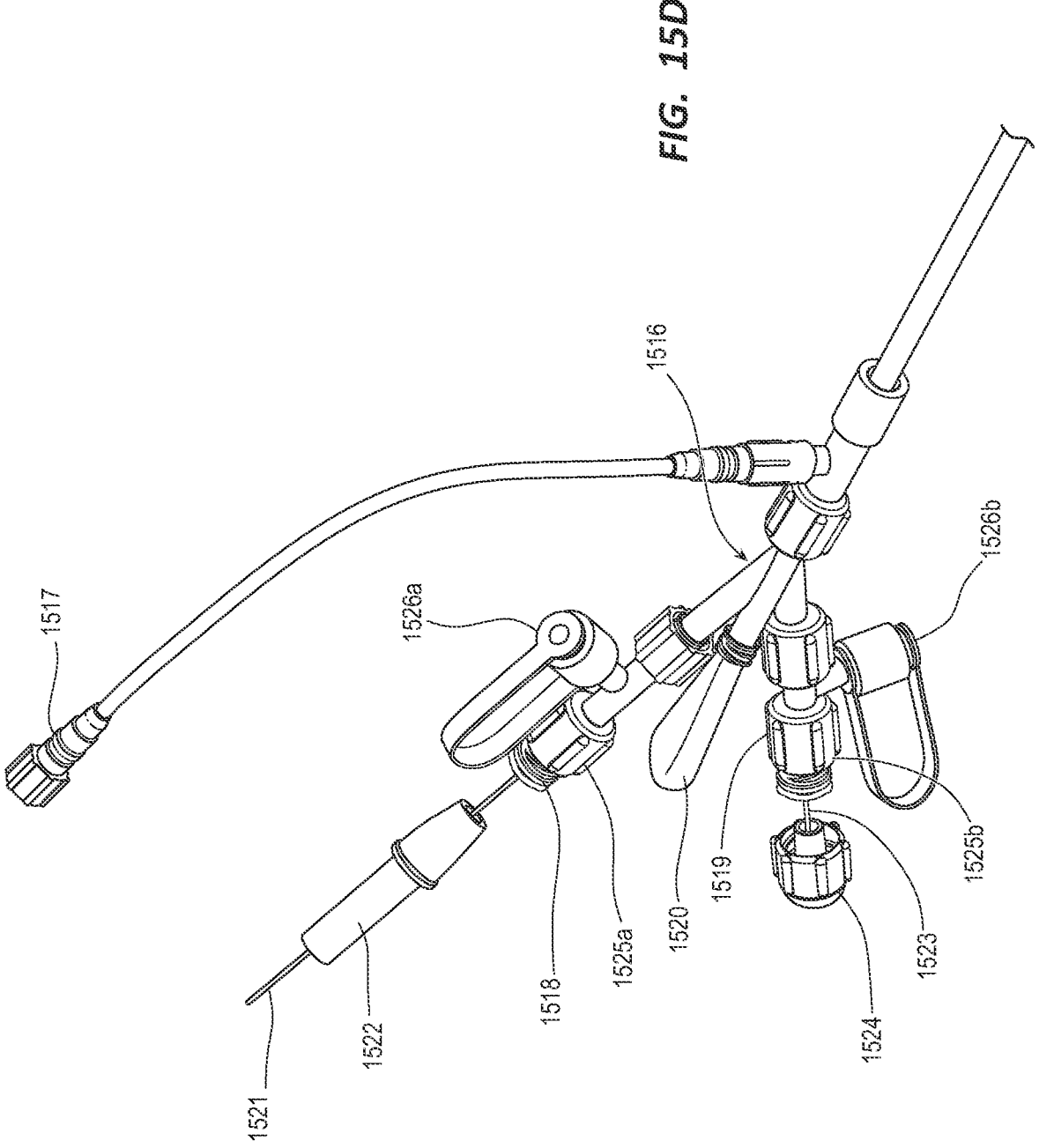
FIG. 15D illustrates a perspective view of a catheter hub of a balloon catheter.

FIGS. 15A-D show perspective views of a balloon catheter described herein. FIG. 15A shows a perspective view of proximal balloon hub (1500). Proximal balloon hub (1500) comprises oval distal opening (1501) that connects to the first balloon and circular opening (1502) that connects to the second, multi-purpose lumen. FIG. 15B shows a perspective view of distal balloon hub (1503). Distal balloon hub (1503) includes oval proximal openings (1504*a-b*) for connecting with the distal tails of the first and second balloon. FIG. 15C shows catheter shaft (1505) comprising proximal shaft (1506) and distal shaft (1507), proximal balloon hub (1508) and distal balloon hub (1509), balloon assembly (1510) comprising first balloon (1511*a*) and second balloon (1511*b*), catheter tip (1512), contralateral guidewire (1513), and tether wire (1514). FIG. 15C also shows protective sleeve (1515) mounted onto proximal shaft (1506). FIG. 15D shows catheter hub (1516) comprising inflation port (1517), contralateral actuator port (1518), tether wire port (1519), and aortic guidewire port (1520). Contralateral actuator wire (1521) exits contralateral actuator port (1518) and connects to actuator handle (1522). Tether wire (1523) exists tether wire port (1519) and connects to tether wire cap (1524), which can be secured onto tether wire port (1519). Tether wire port (1519) and contralateral actuator port (1518) can feature hemostatic seals (1525*ab*) to prevent backflow of blood. Flush ports (1526*a-b*) with removable caps can connect to actuator wire lumen (1528) and tether wire lumen (1529).

Figure 16A:
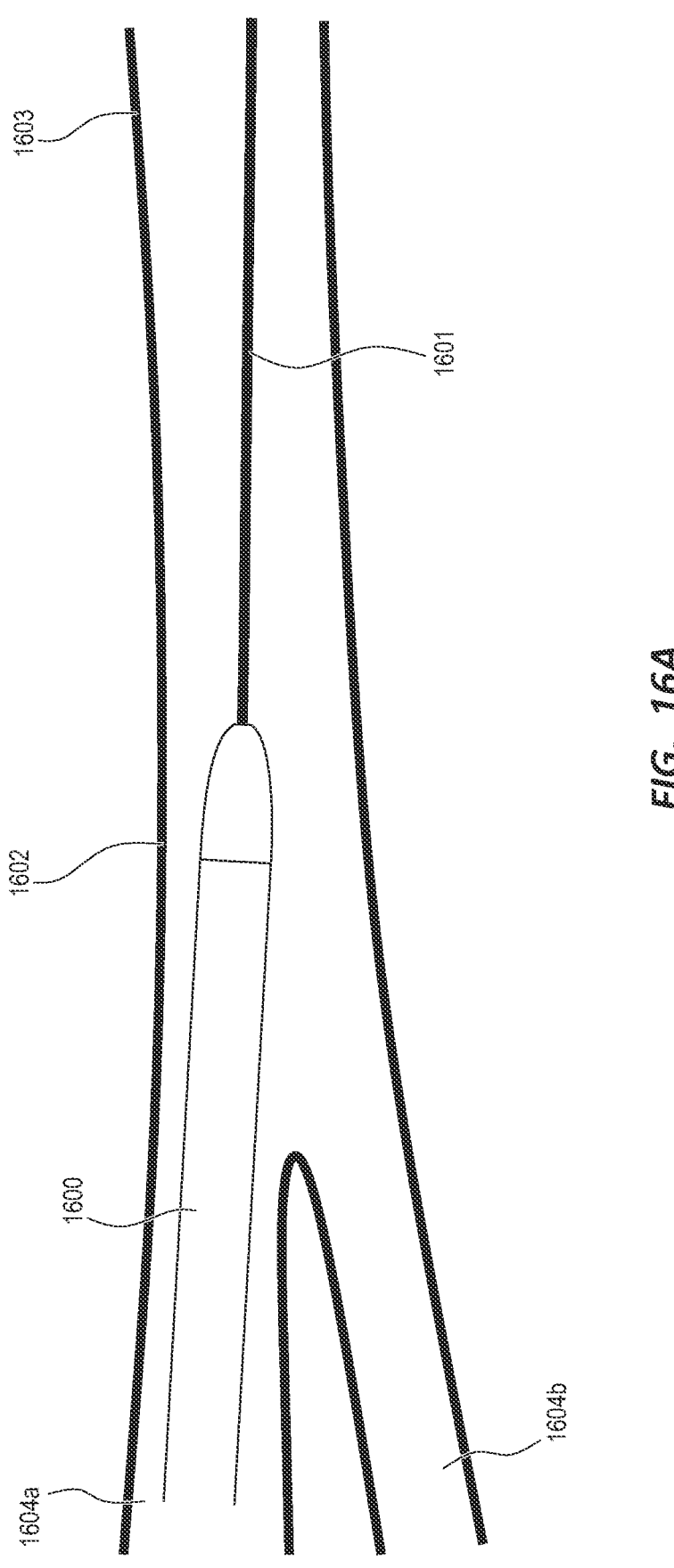
FIG. 16A illustrates advancing a balloon catheter over a guidewire until the balloon assembly is distal to the aorto-iliac bifurcation.
Figure 16B:
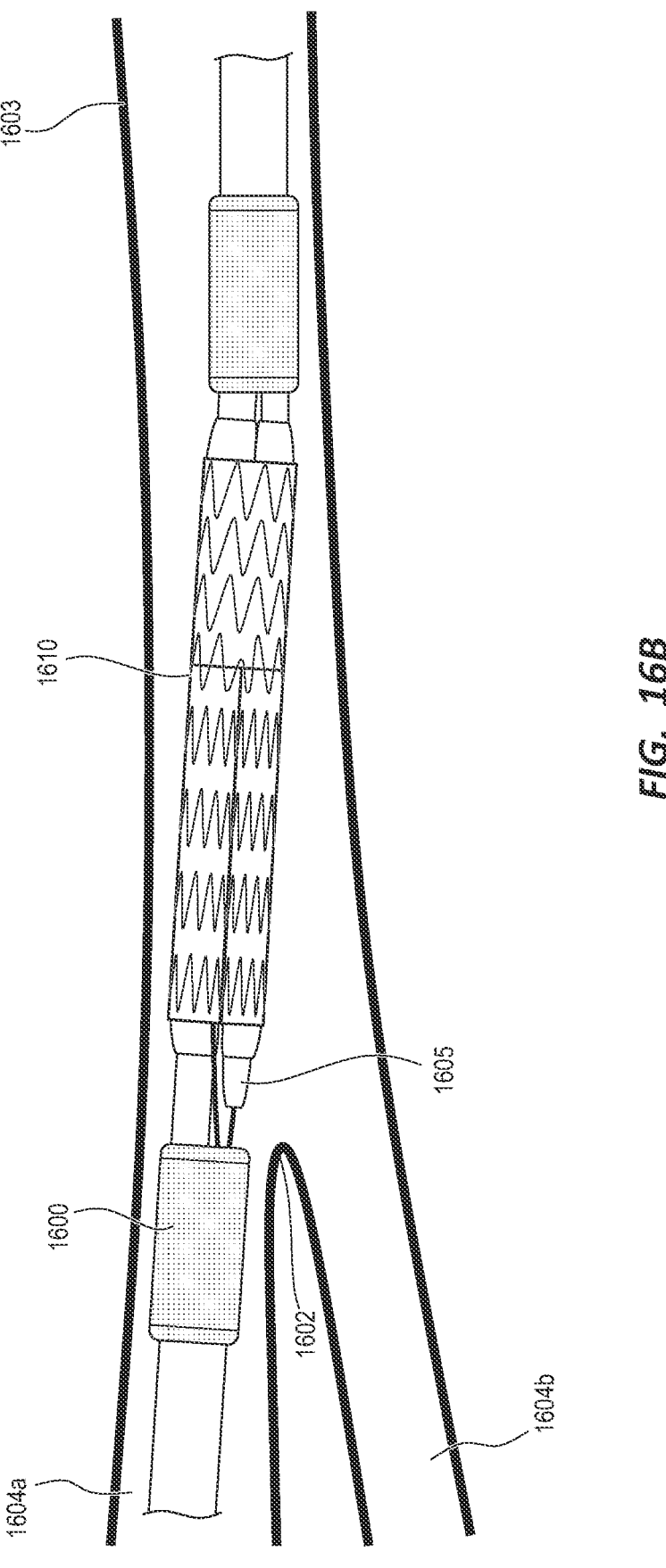
FIG. 16B illustrates advancing the balloon catheter of FIG. 16A past the aorto-iliac bifurcation.

In some embodiments, a method is disclosed for placing a bifurcated stent into the aortoiliac bifurcation using an embodiment of the balloon catheter described herein. FIGS. 16A-J illustrate the individual steps of the method. Balloon catheter (1600) is advanced over aortic guidewire (1601) to aorto-iliac bifurcation (1602) as illustrated in FIG. 16A. Aorto-iliac bifurcation (1602) comprises infrarenal aorta (1603) (e.g. a second vessel), ipsilateral iliac artery (1604*a*) (e.g., a first vessel), and contralateral iliac artery (1604*b*) (e.g., a third vessel). In some embodiments, balloon catheter (1600) can be advanced through an introducer sheath or guide catheter as described in FIGS. 14A-B. Balloon catheter (1600) is advanced until contralateral tip (1605) clears aorto-iliac bifurcation (1602) as illustrated in FIG. 16B.

Figure 16C:
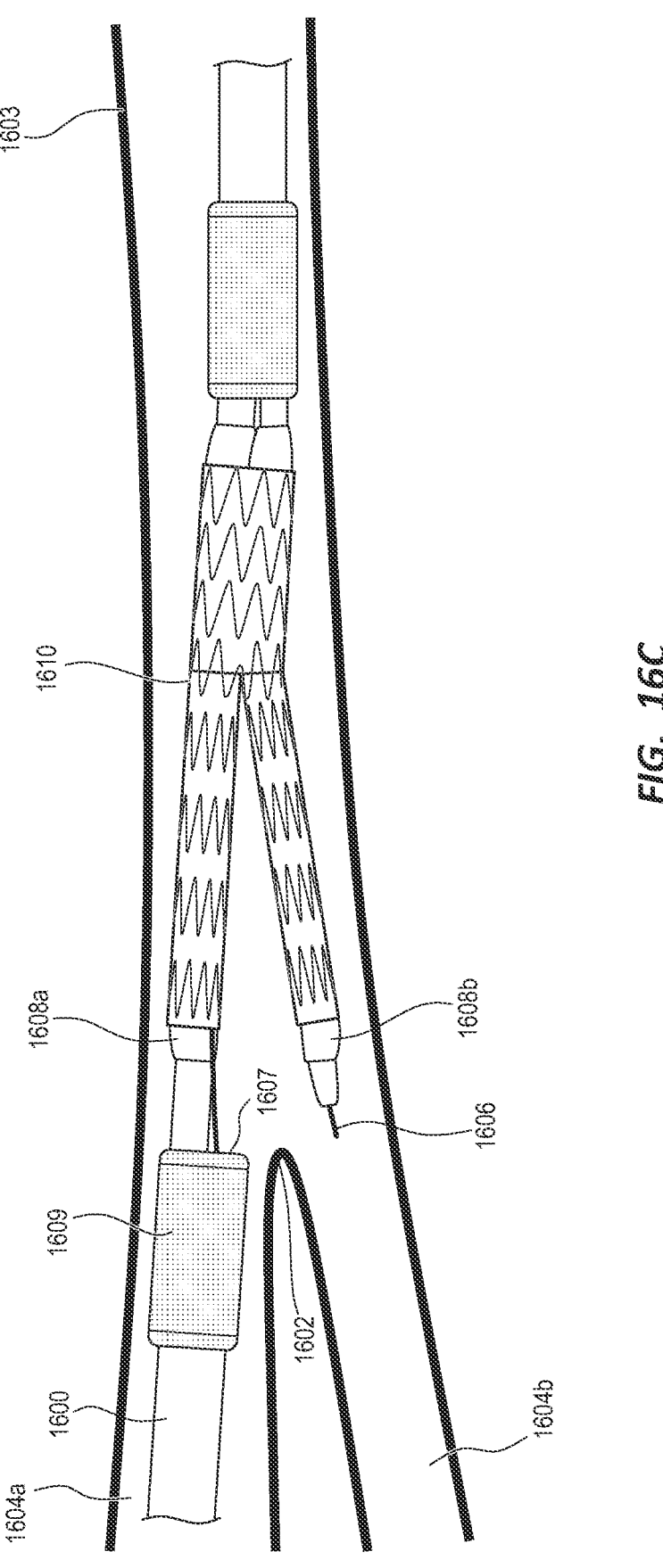
FIG. 16C illustrates releasing the tip of a contralateral guidewire from a multi-purpose lumen.
Figure 16D:
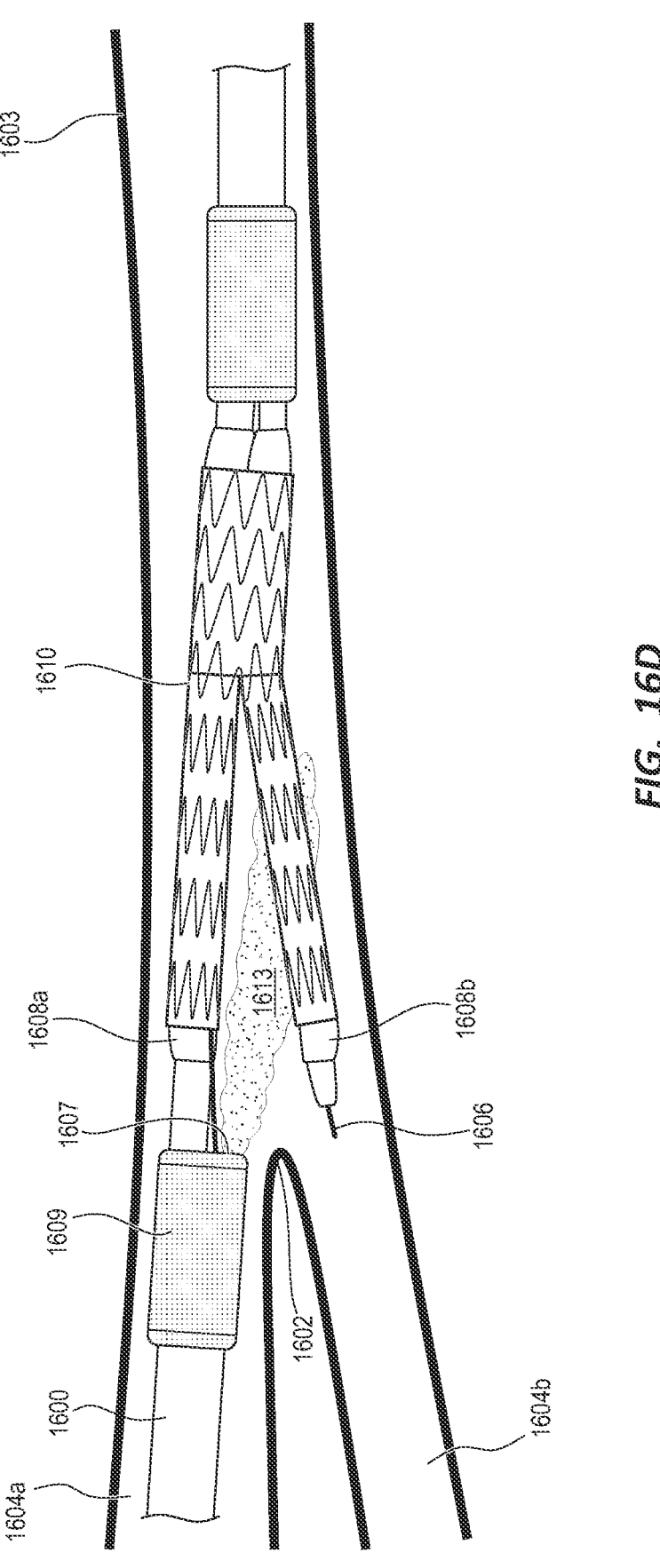
FIG. 16D illustrates ejecting contrast medium to visualize the aorto-iliac bifurcation under fluoroscopy.
Figure 16E:
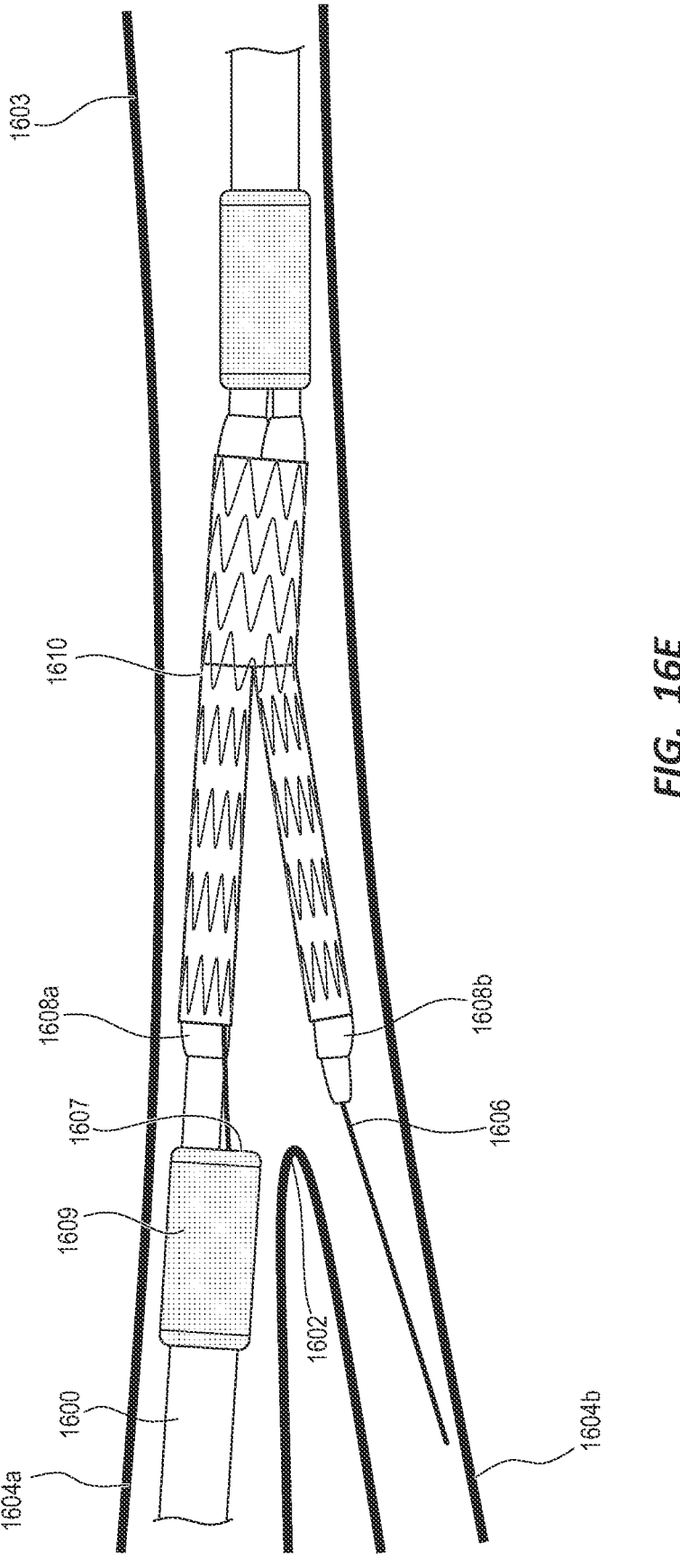
FIG. 16E illustrates advancing the contralateral guidewire tip into the contralateral iliac artery.
Figure 16F:
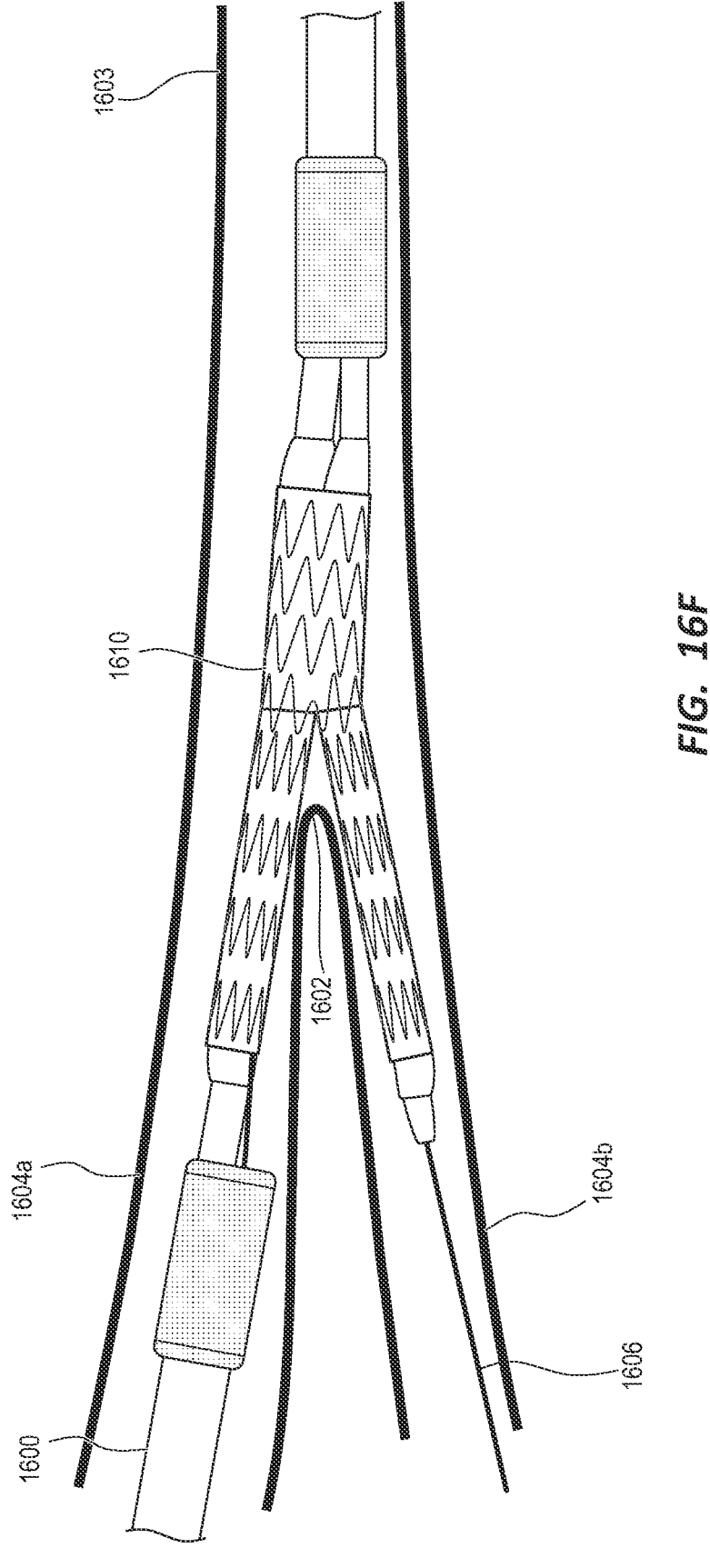
FIG. 16F illustrates advancing the balloon catheter proximally to place a bifurcated stent onto the aorto-iliac bifurcation.
Figure 16G:
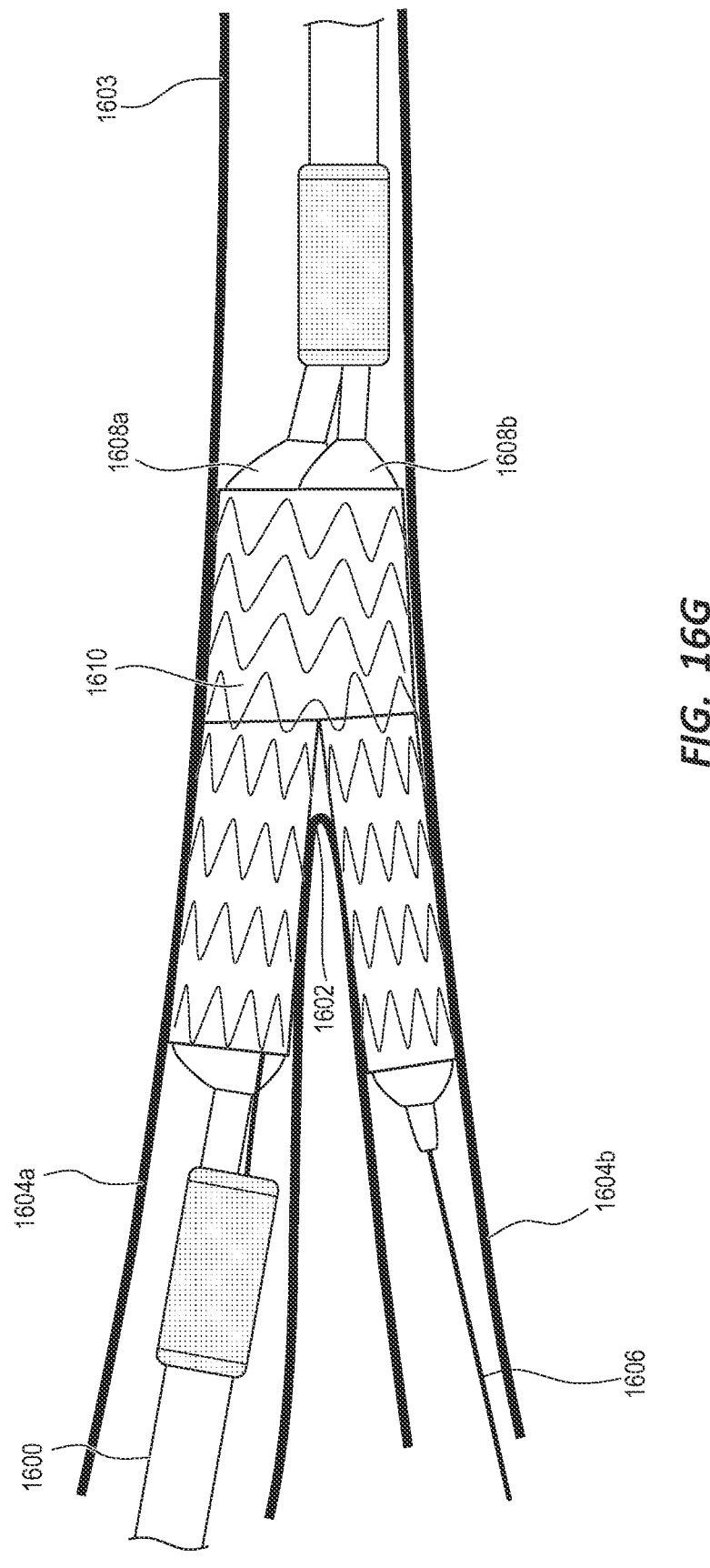
FIG. 16G illustrates injecting fluid into the inflation lumen, inflating the balloon assembly, and deploying the bifurcated stent into the aorto-iliac bifurcation
Figure 16H:
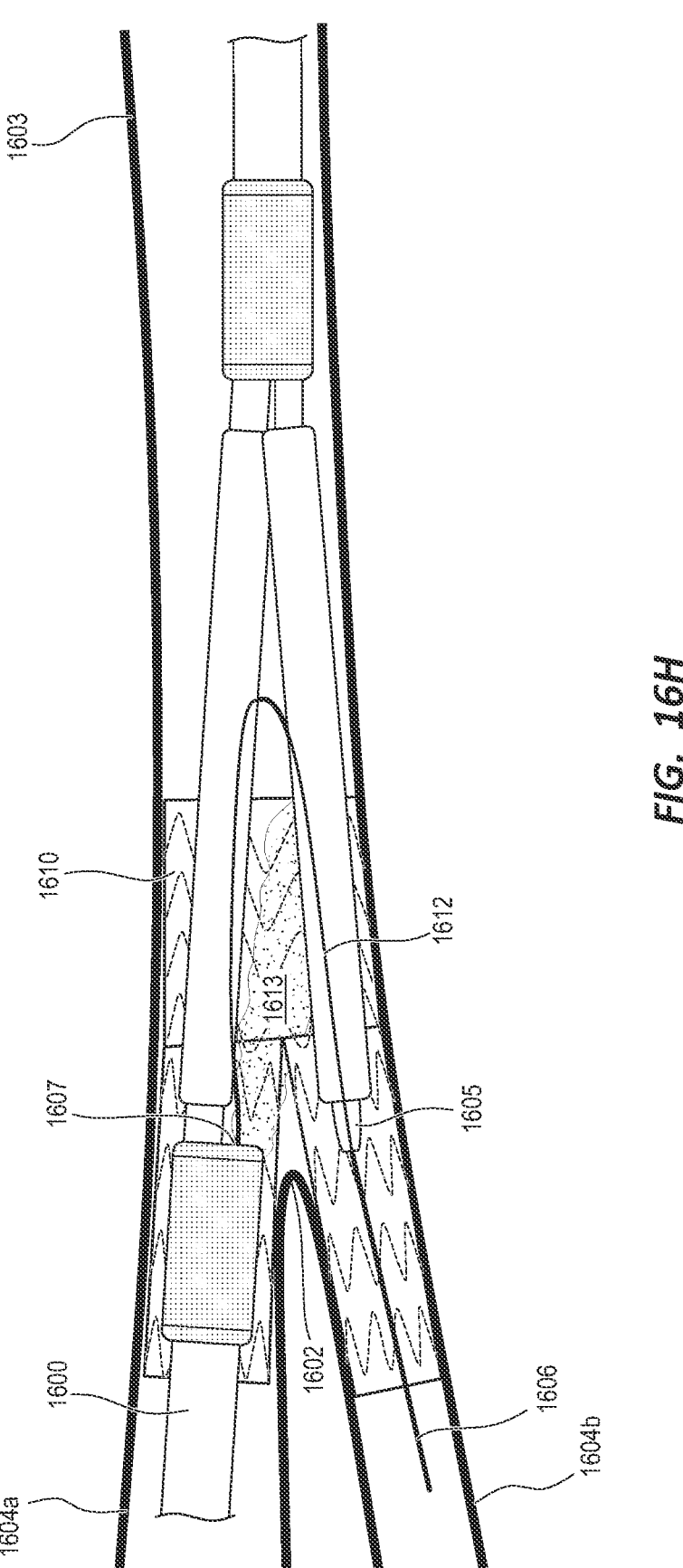
FIG. 16H illustrates withdrawing the fluid from the inflation lumen to deflate the balloon assembly and ejecting contrast medium to confirm lumen patency.
Figure 16I:
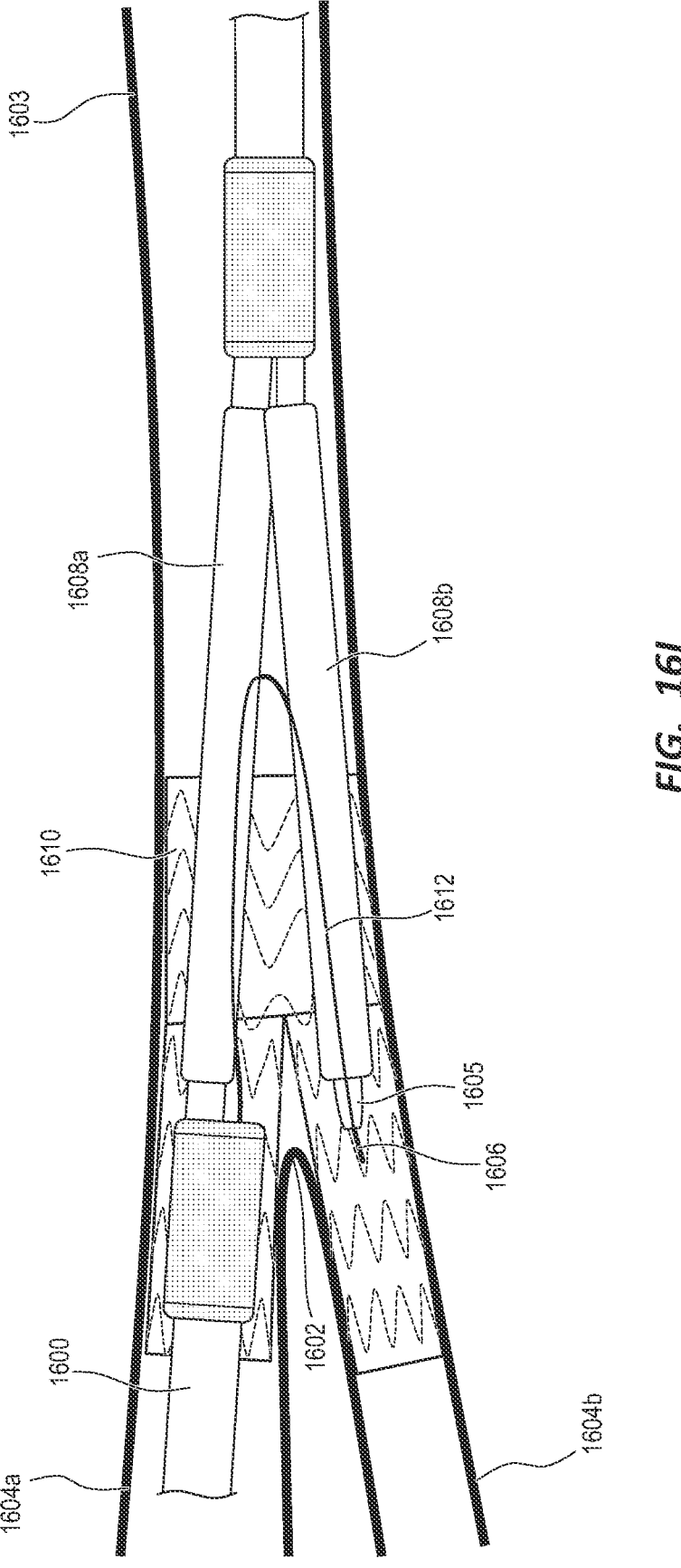
FIG. 16I illustrates retracting the contralateral guidewire into the contralateral balloon shaft and pulling on the tether wire to place the contralateral balloon parallel to the ipsilateral balloon.
Figure 16J:
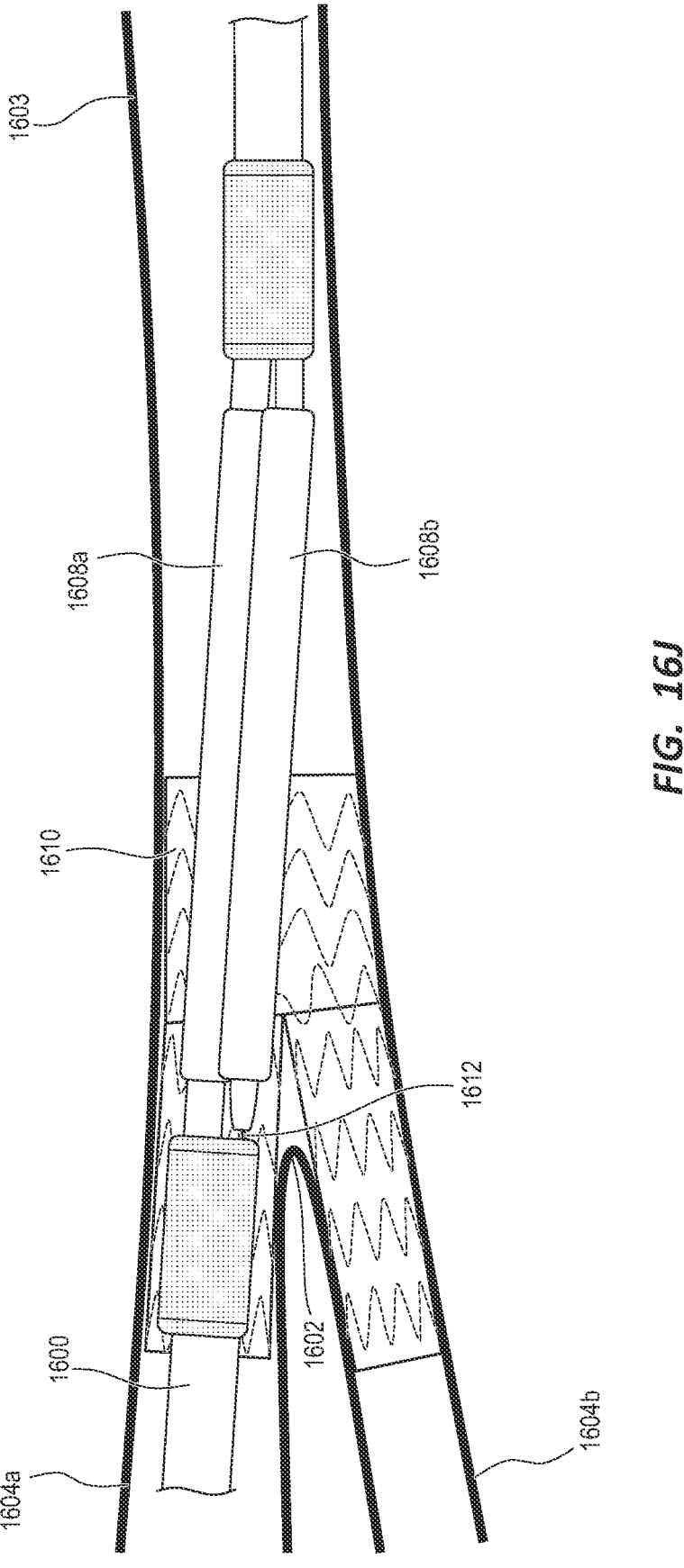
FIG. 16J illustrates removing the balloon catheter from the patient's body

In the next step illustrated in FIG. 16C, contralateral guidewire (1606) is retracted from second lumen (1607) unlocking second (contralateral) balloon (1608*b*) from proximal balloon hub (1609). At this point, contrast medium (1613) can be injected through second lumen (1607) into the blood stream to provide visual guidance for placing contralateral guidewire (1606) into contralateral iliac artery (1604*b*). The injection of contrast medium (1613) is illustrated in FIG. 16D. FIG. 16E shows contralateral guidewire (1606) being advanced into contralateral iliac artery (1604*b*). Once contralateral iliac artery (1604*b*) is cannulated, bifurcated stent (1610) is lowered onto aorto-iliac bifurcation (1602) as illustrated in FIG. 16F. Once proper placement of bifurcated stent (1610) is confirmed, fluid is injected into the inflation lumen. Balloons (1608*a-b*) are inflated as illustrated in FIG. 16G. Bifurcated stent (1610) is expanded against the walls of aorto-iliac bifurcation (1602). To illustrate the subsequent steps, only the posterior half of bifurcated stent (1610) is shown in FIGS. 16H-J. Balloons (1608*a-b*) are deflated. Balloon catheter (1600) is advanced distally until contralateral tip (1605) clears aorto-iliac bifurcation (1602) as shown in FIG. 16H. At this point, contrast medium (1613) can be injected through second lumen (1607) to confirm lumen patency. To remove balloon catheter (1600) from the vasculature, contralateral guidewire (1604) is retracted into the shaft of contralateral balloon (1608*b*) as shown in FIG. 16I. Then, tether wire (1612) is retracted proximally to pull contralateral balloon (1608*b*) against ipsilateral balloon (1608*a*) as shown in FIG. 16J. In this configuration, balloon catheter (1600) can be safely removed from the patient.

Figure 17A:
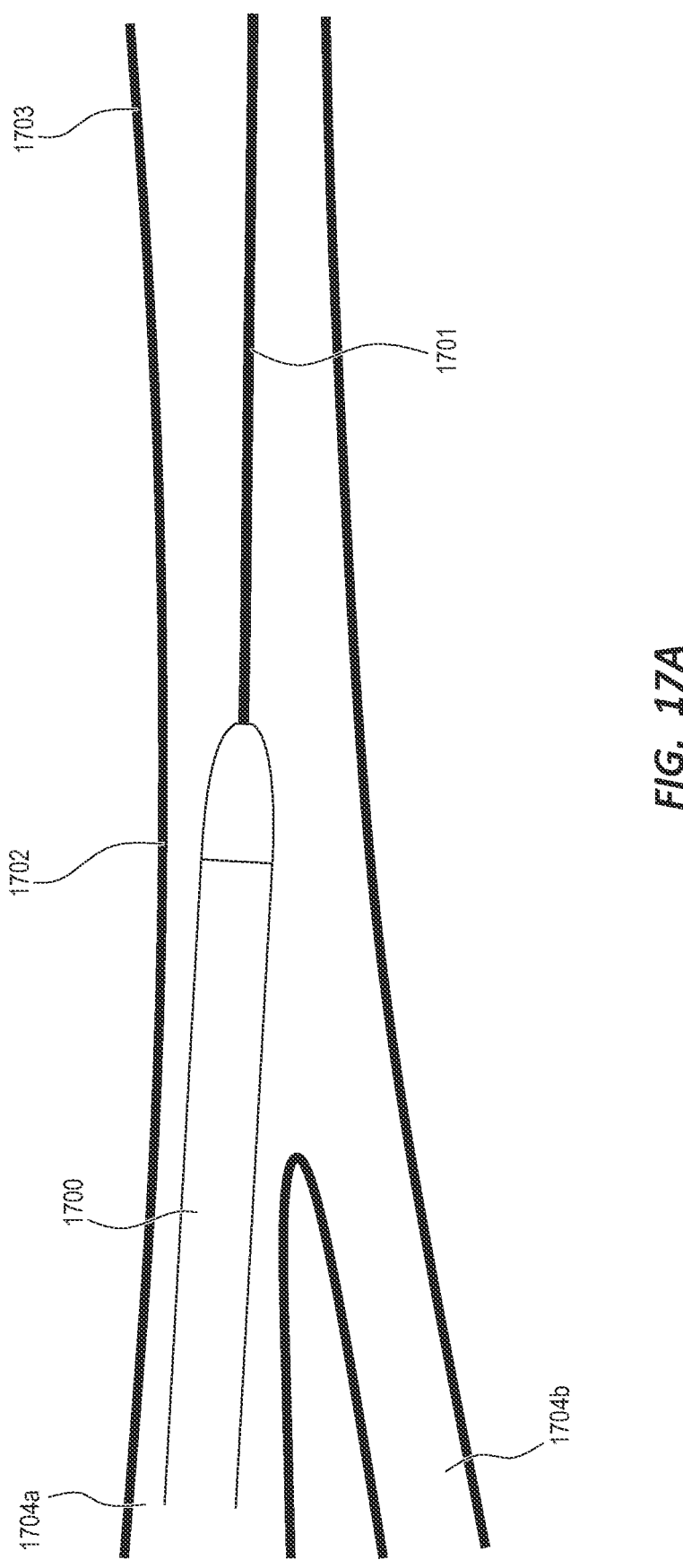
FIG. 17A illustrates advancing the balloon catheter over the guidewire until the balloon assembly is distal to the aorto-iliac bifurcation.
Figure 17B:
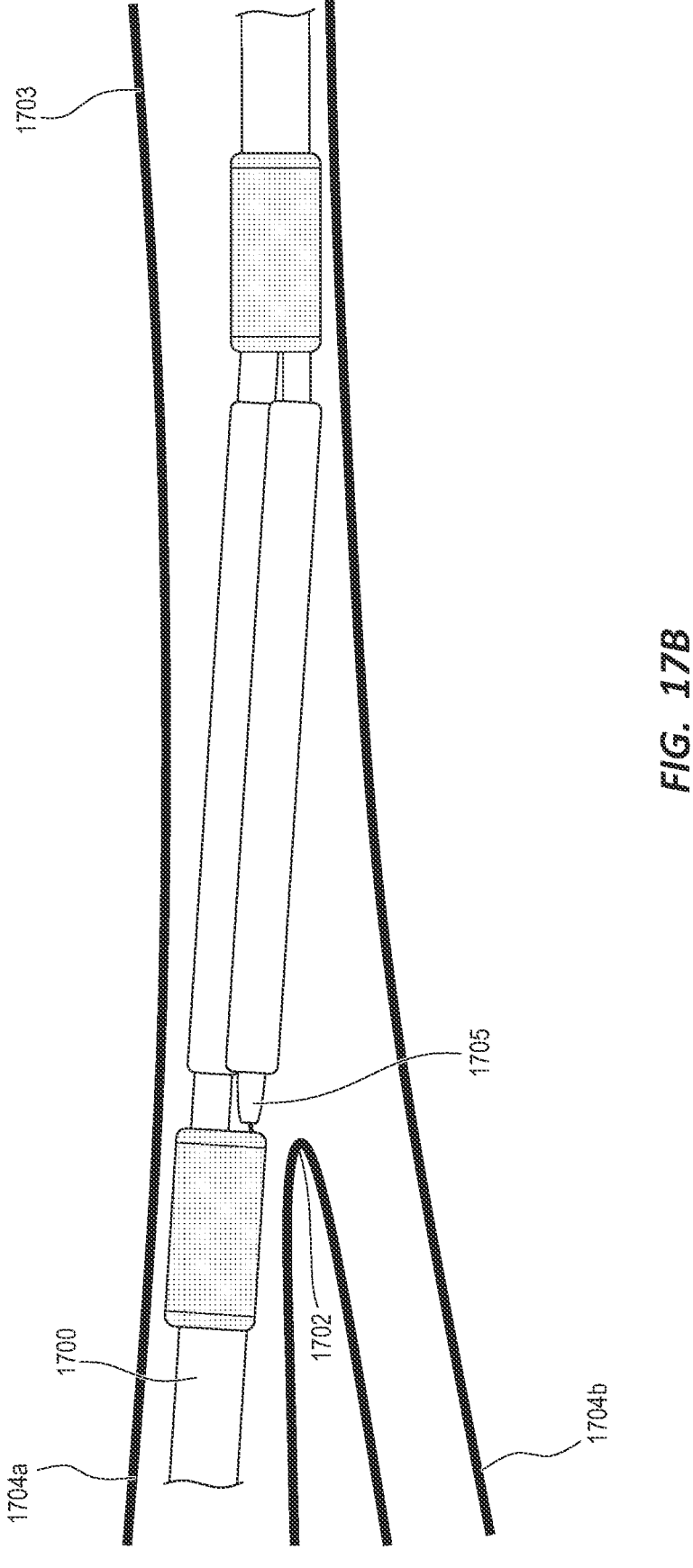
FIG. 17B illustrates advancing the balloon catheter of FIG. 16A past the aorto-iliac bifurcation.
Figure 17C:
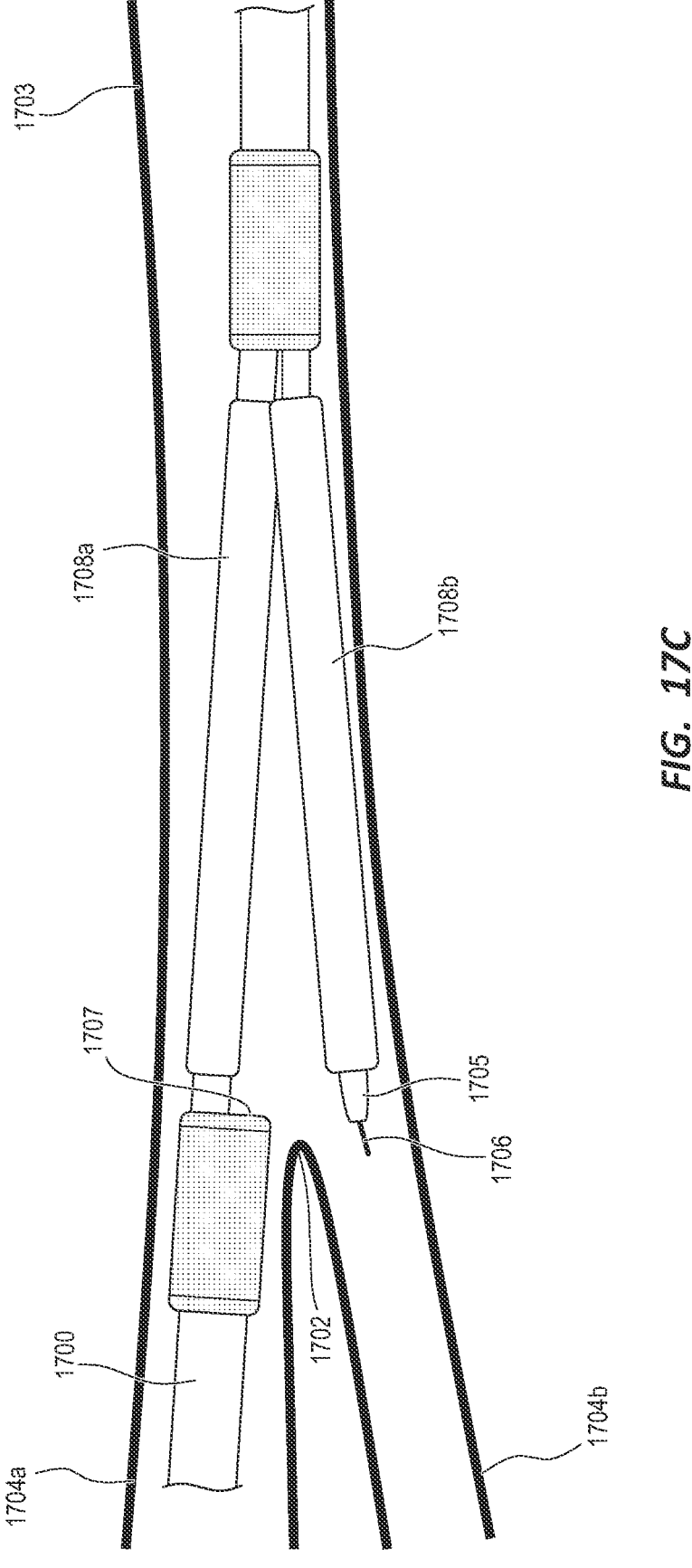
FIG. 17C illustrates releasing a tip of a contralateral guidewire from a multi-purpose lumen.
Figure 17D:
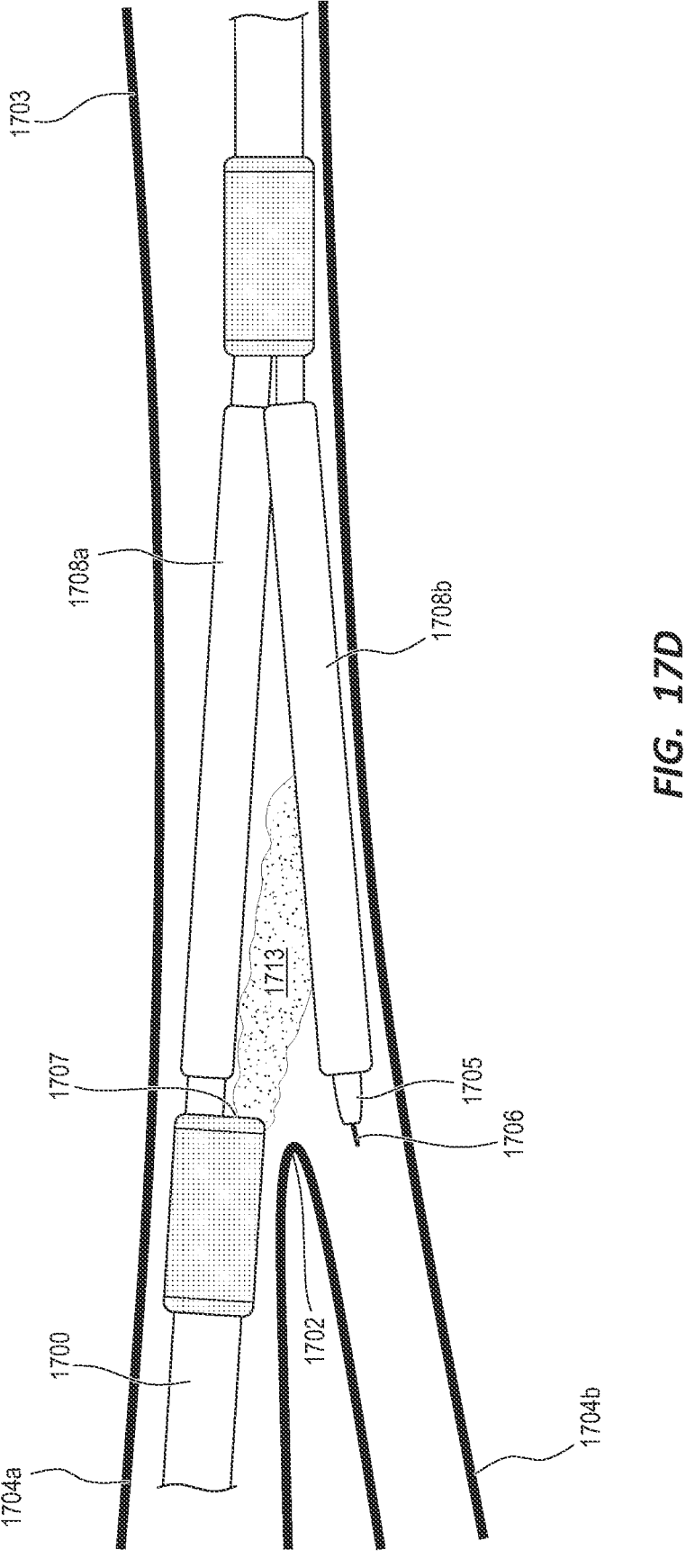
FIG. 17D illustrates ejecting contrast medium through the multi-purpose lumen to visualize the aorto-iliac bifurcation under fluoroscopy.

In another embodiment, a method is disclosed for performing a balloon angioplasty of the aorto-iliac bifurcation using an embodiment of a balloon catheter described herein. FIGS. 17A-M illustrate the individual steps of the method. Balloon catheter (1700) is advanced over aortic guidewire (1701) to aorto-iliac bifurcation (1702) as illustrated in FIG. 17A. Aorto-iliac bifurcation (1702) comprises infrarenal aorta (1703) (e.g., a second vessel), ipsilateral iliac artery (1704*a*) (e.g., a first vessel), and contralateral iliac artery (1704*b*) (e.g., a third vessel). In some embodiments, balloon catheter (1700) can be advanced through an introducer sheath or guide catheter as described in FIGS. 14A-B. Balloon catheter (1700) is advanced until contralateral tip (1705) clears aorto-iliac bifurcation (1702) as illustrated in FIG. 17B. In the next step as illustrated in FIG. 17C, contralateral guidewire (1706) is retracted from second lumen (1707) unlocking second (contralateral) balloon (1708*b*) from second lumen (1707). At this point, contrast medium (1713) can be injected through second lumen (1707) to provide visual guidance for placing contralateral guidewire (1706) into contralateral iliac artery (1704*b*). The injection of contrast medium (1713) is illustrated in FIG. 17D.

Figure 17E:
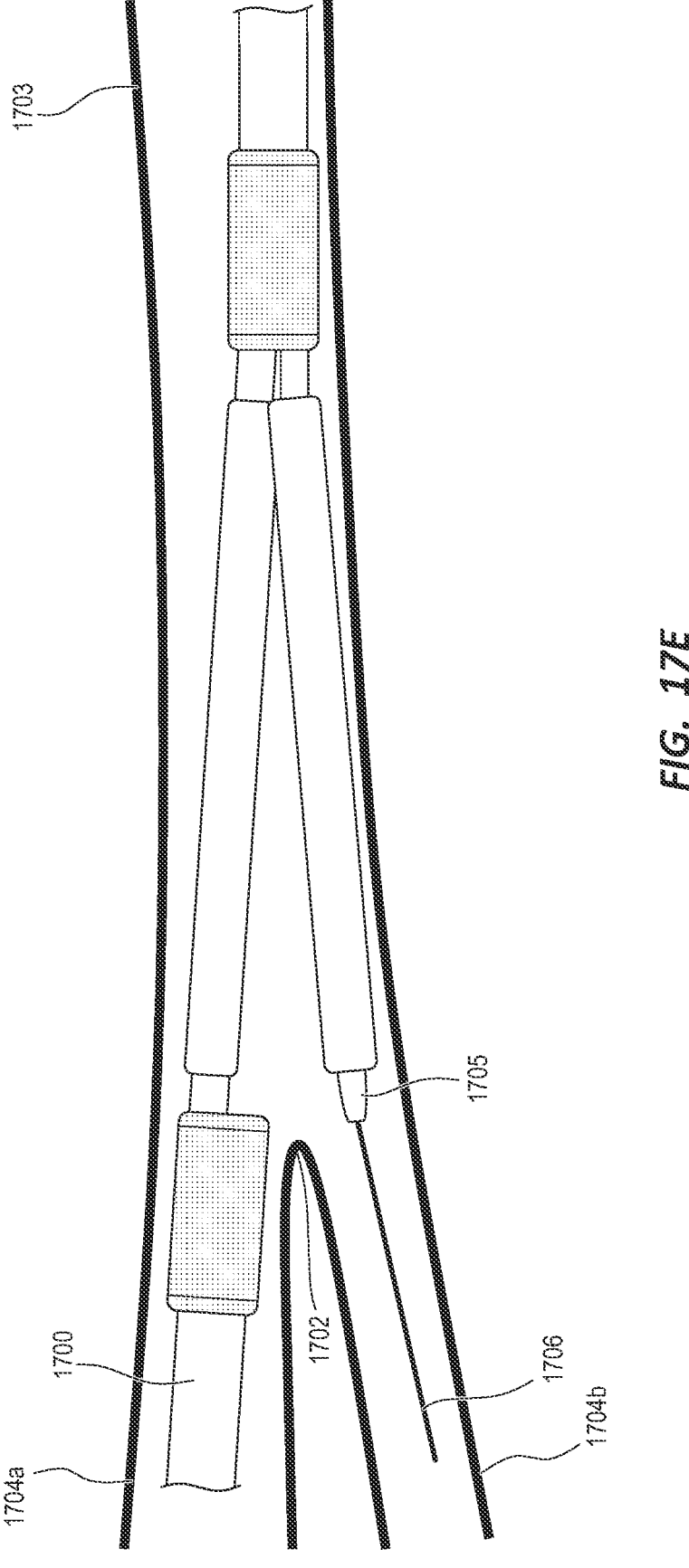
FIG. 17E advancing the contralateral guidewire tip into the contralateral iliac artery.
Figure 17F:
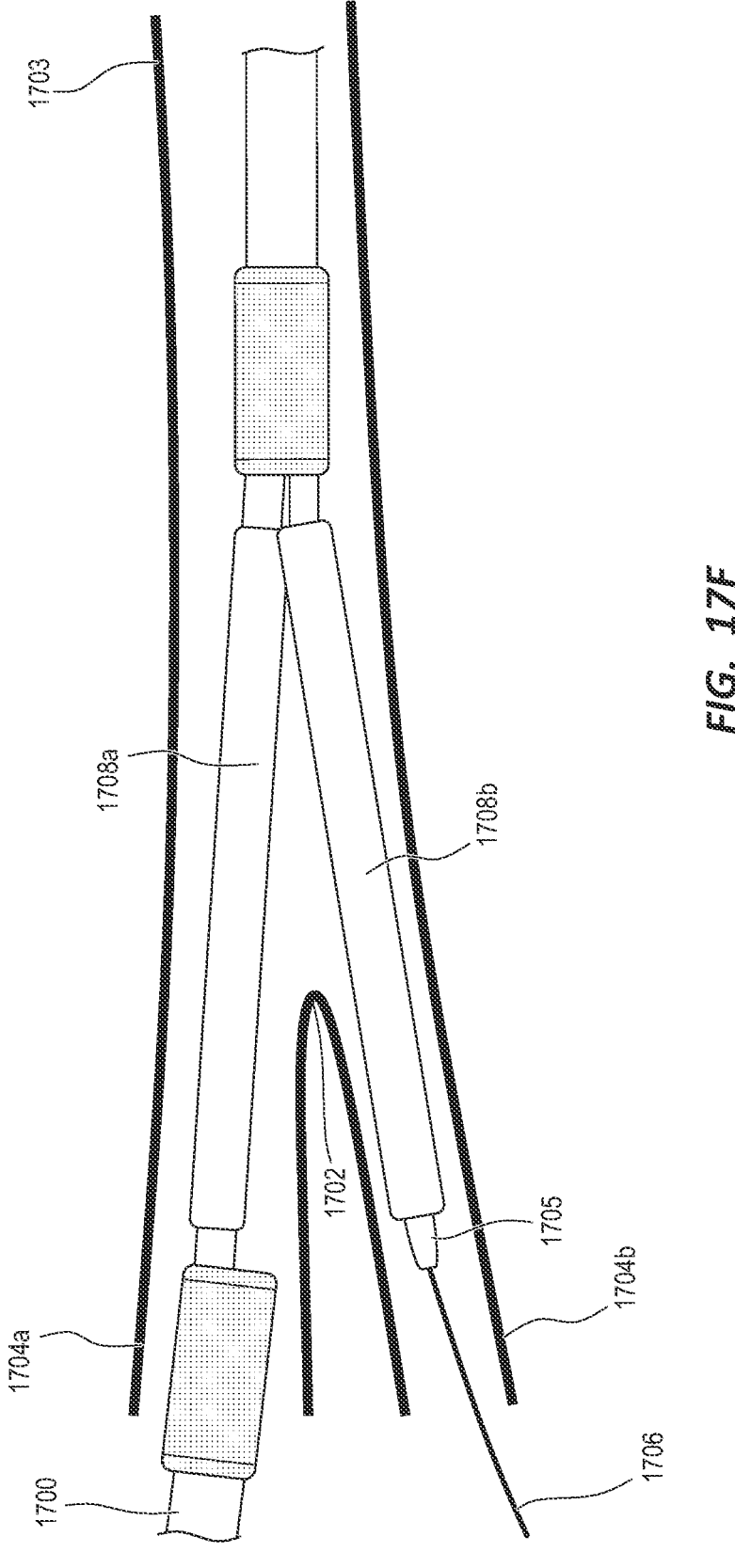
FIG. 17F illustrates advancing the balloon catheter proximally to, at least partially, place the balloon assembly into the branch vessels.
Figure 17G:
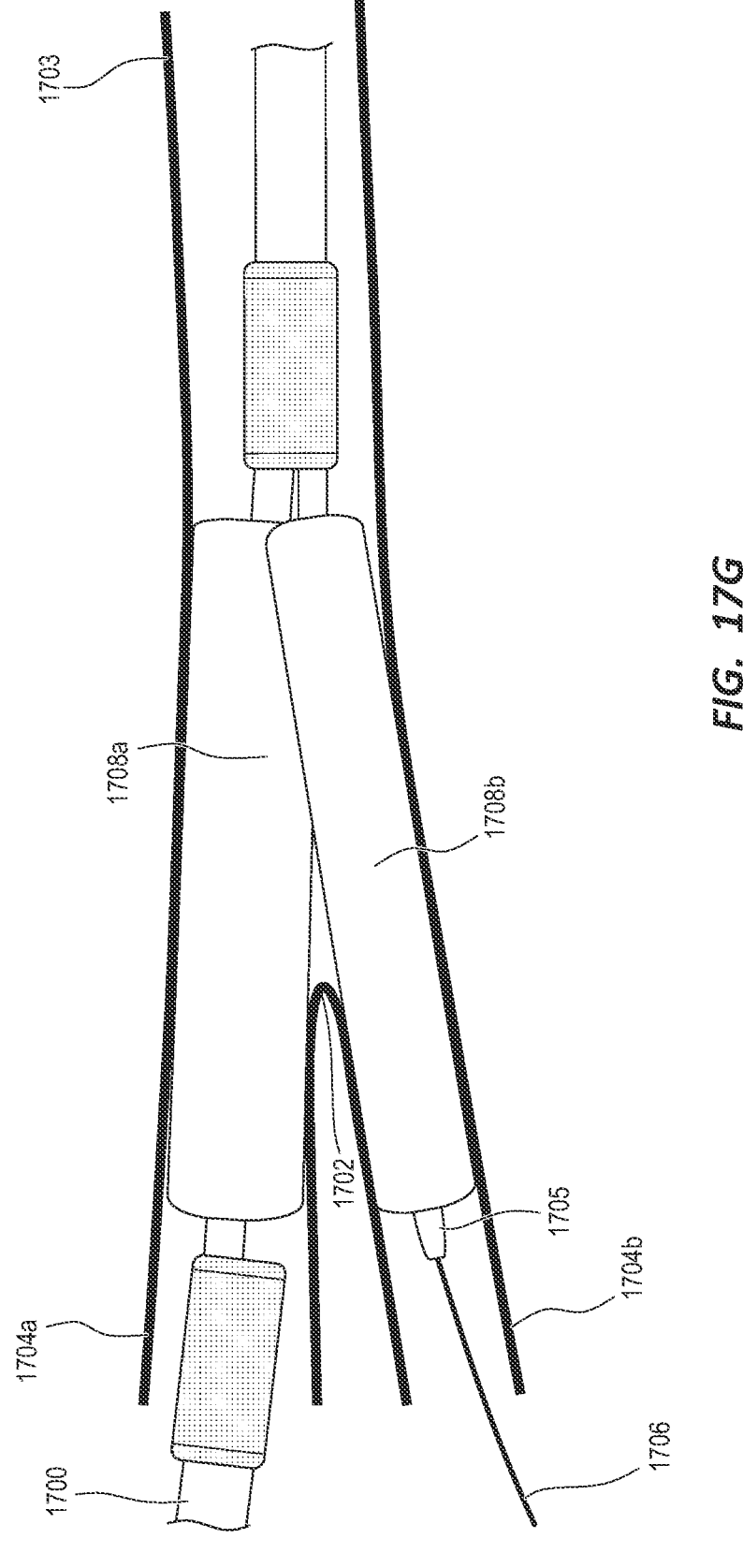
FIG. 17G illustrates injecting fluid into the inflation lumen, inflating the balloon assembly.
Figure 17H:
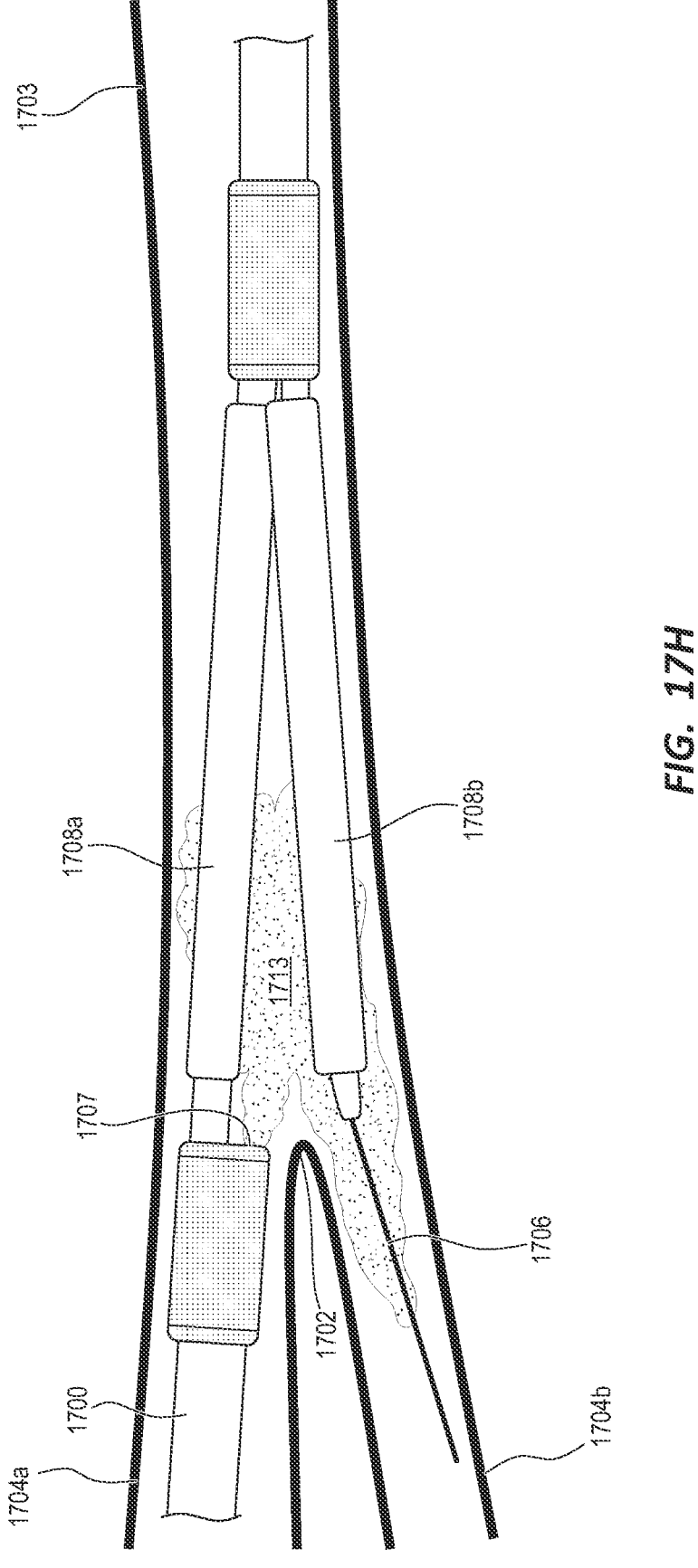
FIG. 17H illustrates withdrawing the fluid from the inflation lumen to deflate the balloon assembly, advancing the balloon catheter distally until the balloon assembly is distal to the aortoiliac bifurcation, and ejecting contrast medium through the multi-purpose lumen to visualize the aorto-iliac bifurcation under fluoroscopy.
Figure 17I:
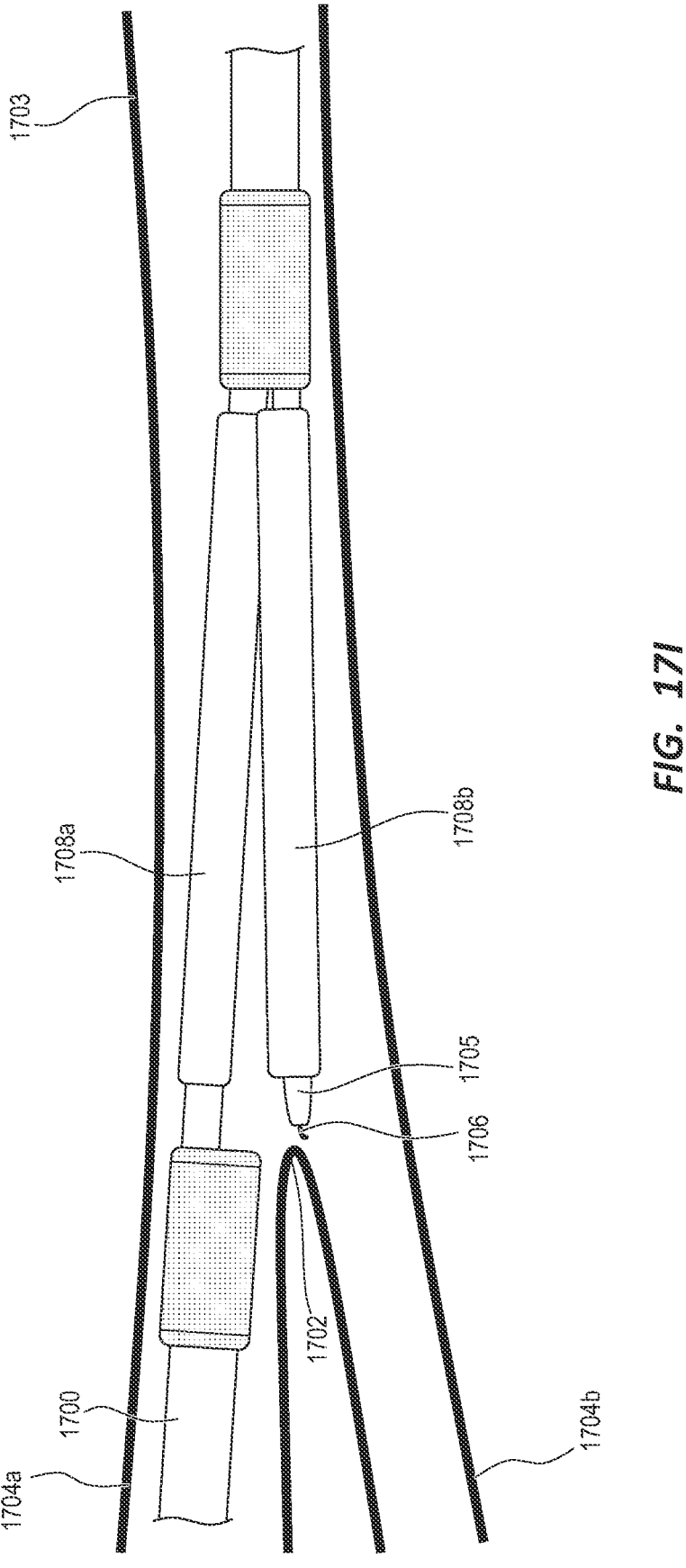
FIG. 17I illustrates retracting the contralateral guidewire into the contralateral balloon shaft.
Figure 17J:
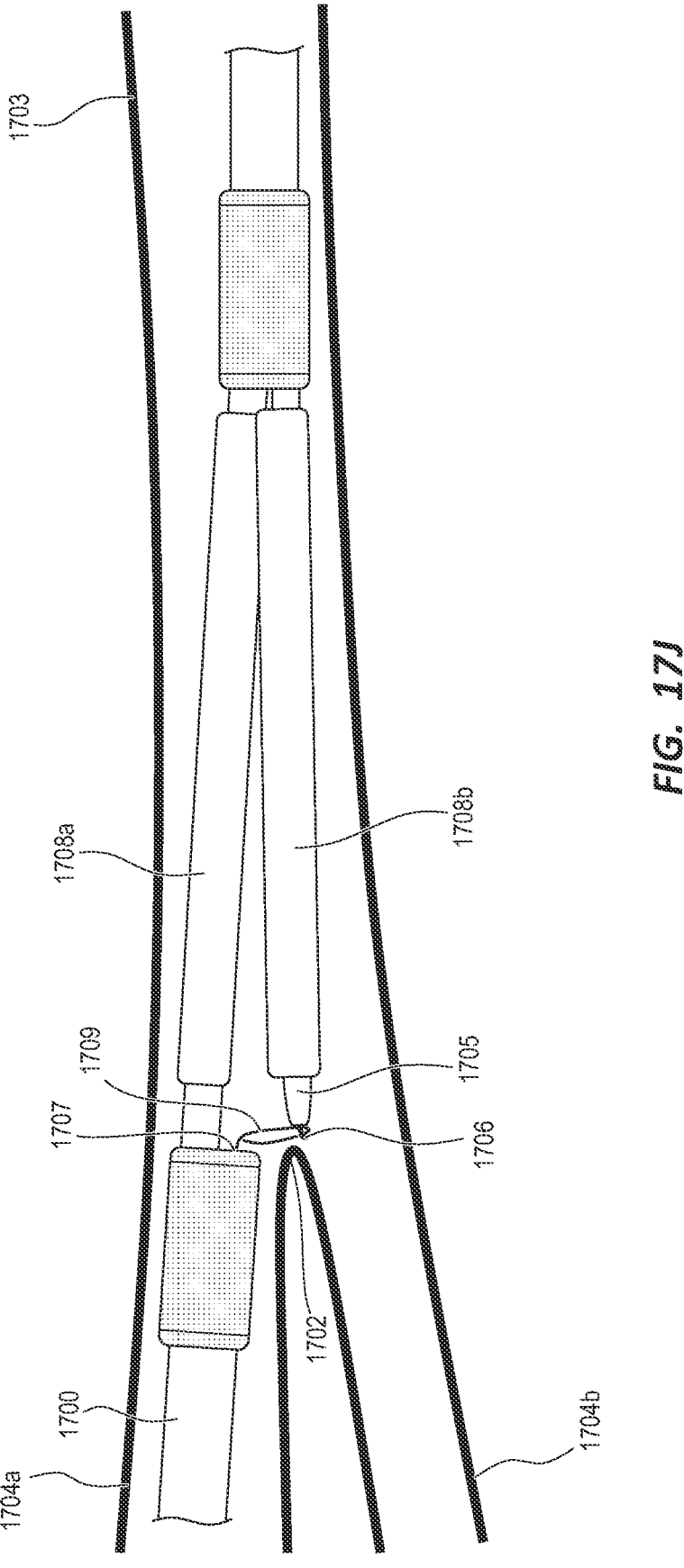
FIG. 17J illustrates advancing a snare though the multi-purpose lumen.
Figure 17K:
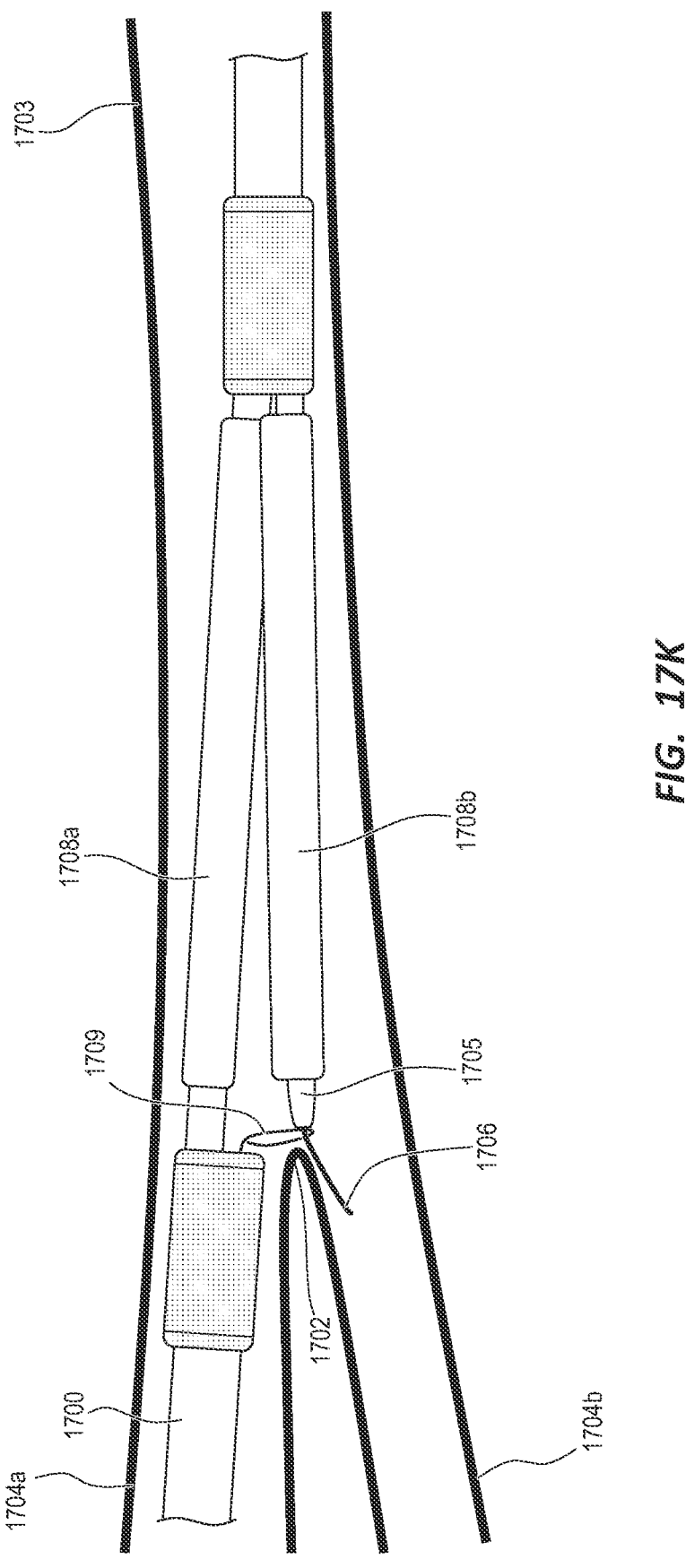
FIG. 17K illustrates capturing the contralateral guidewire tip with the snare.
Figure 17L:
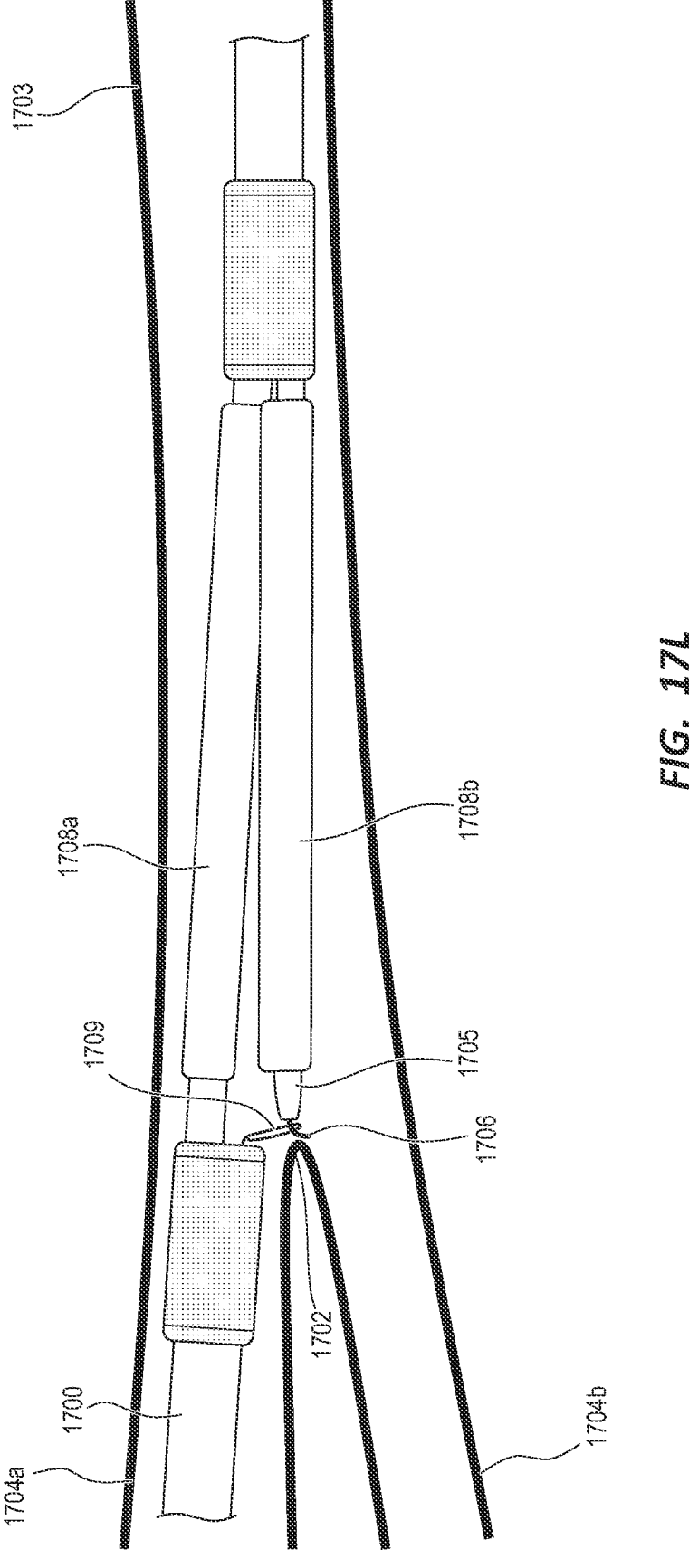
FIG. 17L illustrates pulling the contralateral guidewire tip against or into the proximal balloon hub.

FIG. 17E shows contralateral guidewire (1706) being advanced into contralateral iliac artery (1704*b*). After the contralateral iliac artery (1704*b*) is cannulated, balloons (1708*a-b*) are lowered at least partially into iliac arteries (1704*a-b*) as illustrated in FIG. 17F. When proper placement of balloons (1708*a-b*) has been confirmed, fluid is injected into the inflation lumen. Balloons (1708*a-b*) are inflated (see FIG. 17G). After the angioplasty has been performed, balloons (1708*a-b*) are deflated. Balloon catheter (1700) is advanced distally until contralateral tip (1705) clears aorto-iliac bifurcation (1702) as shown in FIG. 17H. At this point, contrast medium (1713) can be injected through second lumen (1707) to confirm lumen patency. To remove balloon catheter (1700) from the vasculature, contralateral guidewire (1706) is retracted into the shaft of contralateral balloon (1708*b*) as shown in FIG. 17I. Then, snare (1709) is advanced though second lumen (1707). FIG. 17J illustrates snare (1709) exiting second lumen (1707). Contralateral guidewire (1706) is advanced and passed through the loop of snare (1709) as illustrated in FIG. 17K. FIG. 17L shows snare (1709) being closed around the tip of contralateral guidewire (1706). With the help of snare (1709), contralateral guidewire (1706) is pulled against or into second lumen 13
14

Figure 17M:
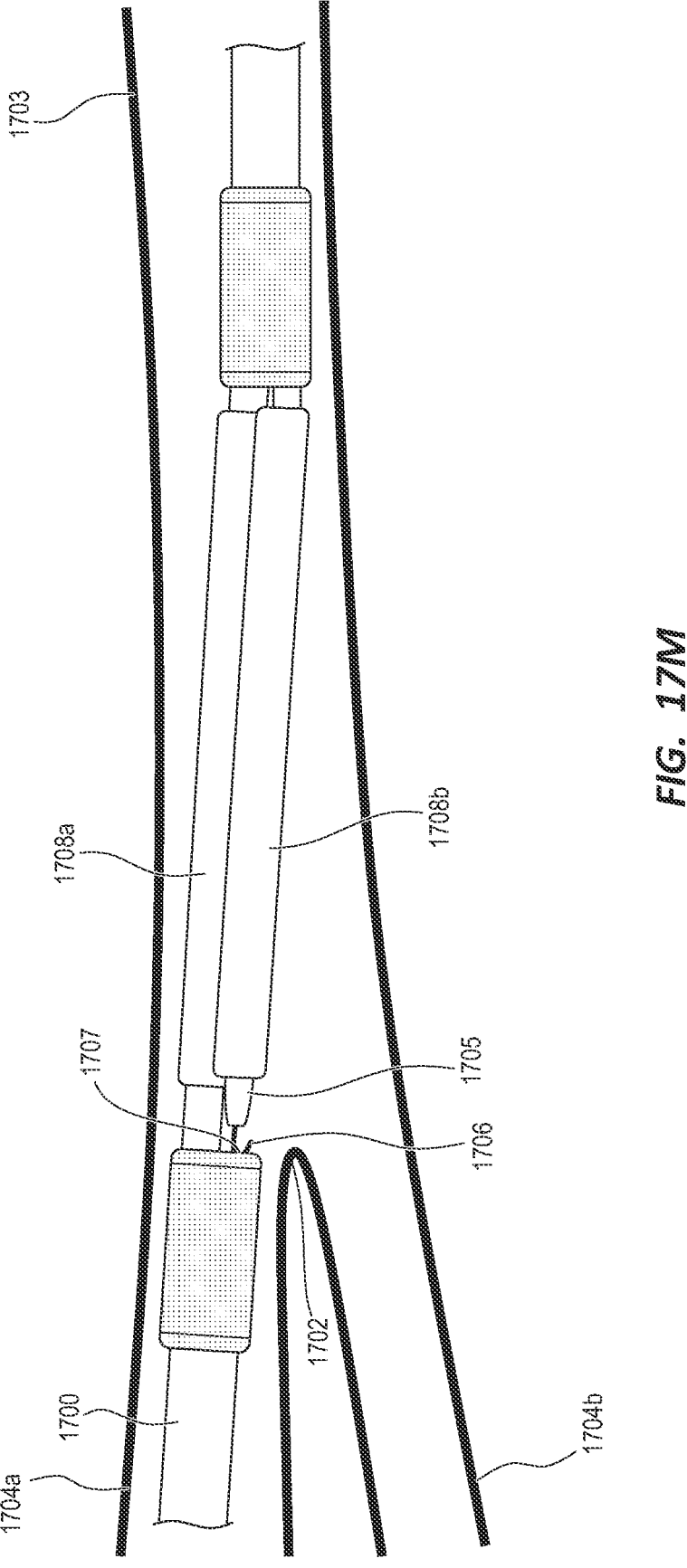
FIG. 17M illustrates pulling the contralateral guidewire tip into the multi-purpose lumen.

(1707) as illustrated in FIG. 17M. In this configuration, balloon catheter (1700) can be safely removed from the patient.

The preceding disclosures are illustrative embodiments. It should be appreciated by those of skill in the art, having the benefit of this disclosure, that the devices, techniques, and methods disclosed herein elucidate representative embodiments that function well in the practice of the present disclosure. However, those of skill in the art should, in light of the present disclosure, appreciate that many changes can be made in the specific embodiments that are disclosed and still obtain a like or similar result without departing from the spirit and scope of the disclosure.

The terms "a" and "an" and "the" and similar referents used in the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments in portions of this disclosure are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Various embodiments are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consist-ing of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed:

1. A balloon catheter for treating a diseased bifurcated blood vessel, the balloon catheter comprising:
   a catheter hub;
   a proximal balloon hub;
   a distal balloon hub;
   a catheter tip;
   a catheter shaft comprising a proximal shaft and a distal shaft, wherein a proximal end of the proximal shaft is connected to the catheter hub and a distal end of the proximal shaft is connected to the proximal balloon hub, a proximal end of the distal shaft is connected to the distal balloon hub and a distal end of the distal shaft is connected to the catheter tip;
   a bifurcated balloon assembly comprising a first balloon and a second balloon, wherein the first balloon and the second balloon are arranged substantially in parallel;
   a first lumen that extends from a first port of the catheter hub through the proximal shaft, the proximal balloon hub, the first balloon, the distal balloon hub, the distal shaft, and the catheter tip; and
   a second lumen that extends from a second port of the catheter hub through the proximal shaft, and the proximal balloon hub to a distal opening in the proximal balloon hub,
   wherein a proximal end of the first balloon is connected to the proximal balloon hub, a distal end of the first balloon is connected to the distal balloon hub, and a distal end of the second balloon is connected to the distal balloon hub.

2. The balloon catheter of claim 1, further comprising a third lumen that extends from a third port of the catheter hub through the proximal shaft, the proximal balloon hub, the first balloon, and the distal balloon hub to a distal opening in the distal balloon hub.

3. The balloon catheter of claim 2, further comprising a fourth lumen that extends from a fourth port of the catheter hub through the proximal shaft, the proximal balloon hub, the first balloon, the distal balloon hub, a cavity of the distal balloon hub, and into the second balloon,
   wherein a portion of the fourth lumen is formed by the proximal shaft.

4. The balloon catheter of claim 3, further comprising a fifth lumen that extends from the distal opening in the distal balloon hub through the distal balloon hub and the second balloon to a contralateral tip of the second balloon.

5. The balloon catheter of claim 4, further comprising a sixth lumen formed by the distal shaft,
   wherein the sixth lumen extends from the proximal end of the distal shaft to the catheter tip.

6. The balloon catheter of claim 5, further comprising a contralateral guidewire assembly comprising:

a first guidewire that extends through the third lumen into the sixth lumen;

a second guidewire that extends from the sixth lumen through the fifth lumen and proximally beyond the contralateral tip of the second balloon; and a connector coupled to the first guidewire and to the second guidewire, the connector is housed within the sixth lumen.

7. The balloon catheter of claim 6, wherein the second guidewire extends into the distal opening of the proximal balloon hub and the second lumen.

8. The balloon catheter of claim 6, wherein a proximal pull on a proximal end of the first guidewire proximally translates the connector and proximally translates the second guidewire.

9. The balloon catheter of claim 6, wherein a distal push on a proximal end of the first guidewire distally translates the connector and distally translates the second guidewire.

10. The balloon catheter of claim 5, further comprising a tether that extends from the second port through the second lumen and out of the distal opening of the proximal balloon hub and configured to connect to the contralateral tip of the second balloon.

11. The balloon catheter of claim 10, wherein a distal end of the tether comprises a loop snare configured to connect to the second guidewire.

12. The balloon catheter of claim 10, further comprising a loop attached at the proximal end of the first balloon, wherein the tether extends out of the second lumen through the loop and is coupled to the contralateral tip of the second balloon.

13. The balloon catheter of claim 5, further comprising:

a first tether that extends from the second port through the second lumen and out of the distal opening of the proximal balloon hub and is coupled to the contralateral tip of the second balloon; and a second tether that extends from the second port through the second lumen and out of the distal opening of the proximal balloon hub and is coupled to the contralateral tip of the second balloon, wherein the first tether wraps clockwise around a proximal portion of the first balloon and the second tether wraps counterclockwise around the proximal portion of the first balloon.

14. A bifurcated stent assembly for placing a bifurcated stent into a diseased bifurcated blood vessel, the bifurcated stent assembly comprising:

a catheter hub;

a proximal balloon hub;

a distal balloon hub;

a catheter tip;

a catheter shaft comprising a proximal shaft and a distal shaft, wherein a proximal end of the proximal shaft is connected to the catheter hub and a distal end of the proximal shaft is connected to the proximal balloon hub, a proximal end of the distal shaft is connected to the distal balloon hub and a distal end of the distal shaft is connected the catheter tip;

a bifurcated balloon assembly comprising a first balloon and a second balloon, wherein the first balloon and the second balloon are arranged substantially in parallel;

a first lumen that extends from a first port of the catheter hub through the proximal shaft, the proximal balloon hub, the first balloon, the distal balloon hub, the distal shaft, and the catheter tip;

a second lumen that extends from a second port of the catheter hub through the proximal shaft, and the proximal balloon hub to a distal opening in the proximal balloon hub; and a bifurcated stent comprising a main body portion, a first branch portion, and a second branch portion, wherein a proximal end of the first balloon is connected to the proximal balloon hub, a distal end of the first balloon is connected to the distal balloon hub, and a distal end of the second balloon is connected to the distal balloon hub, and wherein the main body portion is disposed around distal portions of the first balloon and the second balloon, the first branch portion is disposed around a proximal portion of the first balloon, and the second branch portion is disposed around a proximal portion of the second balloon.

15. The bifurcated stent assembly of claim 14, further comprising a tether that extend through a lumen of the catheter hub through the proximal shaft, and the proximal balloon hub to a distal opening of the proximal balloon hub, wherein the tether extends through the first branch portion and curves into the second branch portion and is coupled to a contralateral tip of the second balloon.

16. A method for placing a bifurcated stent into a diseased bifurcated blood vessel comprising:

advancing a bifurcated stent assembly over a guidewire to the bifurcated blood vessel through a first vessel, the bifurcated blood vessel comprising the first vessel, a second vessel, and a third vessel, the bifurcated stent assembly comprising:

a catheter hub;

a proximal balloon hub;

a distal balloon hub;

a catheter tip;

a catheter shaft comprising a proximal shaft and a distal shaft, wherein a proximal end of the proximal shaft is connected to the catheter hub and a distal end of the proximal shaft is connected to the proximal balloon hub, a proximal end of the distal shaft is connected to the distal balloon hub and a distal end of the distal shaft is connected the catheter tip;

a bifurcated balloon assembly comprising a first balloon and a second balloon, wherein the first balloon and the second balloon are arranged substantially in parallel, and wherein a proximal end of the second balloon has a contralateral tip;

a first lumen that extends from a first port of the catheter hub through the proximal shaft, the proximal balloon hub, the first balloon, the distal balloon hub, the distal shaft, and the catheter tip;

a second lumen that extends from a second port of the catheter hub through the proximal shaft, and the proximal balloon hub to a distal opening in the proximal balloon hub; and a bifurcated stent comprising a main body portion, a first branch portion, and a second branch portion, wherein a proximal end of the first balloon is connected to the proximal balloon hub, a distal end of the first balloon is connected to the distal balloon hub, and a distal end of the second balloon is connected to the distal balloon hub, and wherein the main body portion is disposed around distal portions of the first balloon and the second balloon, the first branch portion is disposed around a proximal portion of the first balloon, and the second branch portion is disposed around a proximal portion of the second balloon;

advancing the bifurcated stent assembly into the second vessel until the contralateral tip clears the bifurcated blood vessel;

retracting a contralateral guidewire from the proximal balloon hub, the contralateral guidewire extends from the distal shaft through the distal balloon hub, the second balloon, the contralateral tip, and the proximal balloon hub;

extending the contralateral guidewire into the third vessel adjacent to the first vessel and the second vessel;

advancing the second balloon and the second branch portion into the second vessel and simultaneously retracting the first balloon and the first branch portion into the first vessel, wherein the first balloon and the second balloon are not parallel;

inflating the first balloon and the second balloon to expand the bifurcated stent against walls of the first vessel, the second vessel, and the third vessel;

deflating the first balloon and the second balloon;

advancing the first balloon and the second balloon into the second vessel;

pulling the second balloon against the first balloon so that the first balloon and the second balloon are substantially parallel; and retracting the bifurcated stent assembly from the first vessel.

17. The method of claim 16, further comprising injecting contrast medium through the proximal balloon hub into the second vessel after the contralateral tip clears the bifurcated blood vessel.

18. The method of claim 16, further comprising injecting contrast medium through the proximal balloon hub into the second vessel after the bifurcated stent is deployed.

\* \* \* \* \*